US008586718B2

(12) United States Patent
Benson et al.

(10) Patent No.: US 8,586,718 B2
(45) Date of Patent: Nov. 19, 2013

(54) MULTI-CHROMOPHORIC QUENCHER CONSTRUCTS FOR USE IN HIGH SENSITIVITY ENERGY TRANSFER PROBES

(75) Inventors: Scott C. Benson, Alameda, CA (US); Steven M. Menchen, Fremont, CA (US); Krishna G. Upadhya, Union City, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 1209 days.

(21) Appl. No.: 11/226,069

(22) Filed: Sep. 14, 2005

(65) Prior Publication Data
US 2006/0063186 A1 Mar. 23, 2006

Related U.S. Application Data

(60) Provisional application No. 60/609,273, filed on Sep. 14, 2004.

(51) Int. Cl.
C09B 62/83 (2006.01)
C09B 35/037 (2006.01)

(52) U.S. Cl.
USPC .......................................... 534/831; 534/832

(58) Field of Classification Search
None
See application file for complete search history.

(56) References Cited

U.S. PATENT DOCUMENTS

| | | | |
|---|---|---|---|
| 5,795,729 A | 8/1998 | Lee | |
| 6,150,097 A * | 11/2000 | Tyagi et al. | 435/6 |
| 6,323,337 B1 | 11/2001 | Singer et al. | |
| 6,790,945 B2 * | 9/2004 | Lukhtanov et al. | 536/23.1 |
| 7,019,129 B1 * | 3/2006 | Cook et al. | 536/26.6 |
| 7,153,654 B2 * | 12/2006 | Wei et al. | 435/6 |
| 7,601,498 B2 * | 10/2009 | Mao et al. | 435/6 |
| 2005/0233332 A1 | 10/2005 | Collis | |
| 2006/0135374 A1 * | 6/2006 | Cooper et al. | 508/150 |

FOREIGN PATENT DOCUMENTS

| | | | |
|---|---|---|---|
| EP | 1 586 662 A1 | 10/2005 | |
| JP | 57-185352 | * 11/1982 | |
| WO | WO 97/28277 A1 | 8/1997 | |
| WO | WO 00/64988 | 11/2000 | |
| WO | WO 2004/024946 A1 | 3/2004 | |
| WO | WO 2005/071115 | * 8/2005 | |

OTHER PUBLICATIONS

Wolski et al., "Optimization of the Extraction Conditions of Amino Acid Dabsyl Derivatives", Chemical Abstracts, 100:131818, 1984.*
Lin et al., "Debsyl Chloride: its synthesis characterization and application in amino acid and amine microanalysis", Chemical Abstracts, 106:175877, 1987.*
Krause et al., "Simultaneous Determination of Amino Acids and Biogenic Amines by Reversed-Phase High-Performance Liquid Chromatography of the Dabsyl Derivatives", Journal of Chromatography A, 715, 67-79, 1995.*
Sapsford et al. "Materials for Fluorescence Resonance Energy Transfer Analysis: Beyond Traditional Donor-Acceptor Combinations", Angewandte Chemie International Edition, 45, 4562-4588, 2006.*
Hubalek et al., "Synthesis and Characterization of a Collagen Model-O-Phosphoohydroxylysine-Containing Peptide", Analytical Biochemistry, 306(1), 124-134, 2002.*
Hubalek et al., "Synthesis and Characterization of a Collagen Model-O-Phosphoohydroxylysine-Containing Peptide", Chemical Abstracts, 137;279447, 2002.*
Archut et al., "Azobenzene-Functionalized Cascade Molecules: Photoswitchable Supramolecular Systems", Chem. Eur. J., 4(4), 699-706, 1998.*
Dirksen et al., "Photoactivity and pH Sensitivity of Methyl Orange Functionalized Poly(Propyleneamine) Dendrimers", Macromolecules, 35, 2743-2747, 2002.*
Yamamoto et al., "Photoresponsive Peptide and Polypeptide Systems. Part 7. Reversible Chiral Photochromism and Solubility Change of Azo Aromatic L-Lysine Related Compounds", Journal of the Chemical Society, Perkin Transactions 2, Physical Organic Chemistry, 10, 1477-1482, 1989.*
Lewandowsky, et al. Angewandte Makromolekulare Chemie, 197:159 (1992).*
Peters, et al., J. Chem. Soc., pp. 2101-2110 (1953).*
Ujiie, et al., Chem. Lett. 12:2217 (1989).*
Grant & Hackh's Chemical Dictionary, 5th ed., eds. Grant, R. and Grant C., front matter and . 228 (1987).*
Yang, C.J., et al,"Molecular Assembly of Superquenchers in Signaling Molecular Interactions", J. Am. Chem. Soc., 2005, 127, 12772-12773, and Supporting Information, pp. S1-S5.

(Continued)

Primary Examiner — Michael Barker

(57) ABSTRACT

Dark quencher constructs, termed "multi-chromophoric quenchers" are described herein that comprise at least two dark quenching moieties, which can be the same or different, linked together by at least one multivalent linking moiety. The structure of the multi-chromophoric quenchers can be varied to selectively enhance quenching within a specific range of reporter emission wavelengths. This can be accomplished by linking together, into a single molecule, two or more identical quenchers, by reacting the quenchers with a multivalent linker. The structure of the multi-chromophoric quencher can also be varied to quench a broader range of reporter emission wavelengths than previously possible. This can be accomplished by linking together, into a single molecule, two or more different quenchers, by reacting the quenchers with a multivalent linker. The structure of the multi-chromophoric quencher can also be varied to simultaneously broaden the absorption range and increase the total absorption within the absorption range. This can be done by combining the two concepts described above. In other words, multiple types of quenching moieties can be employed to increase the absorption range and a multiple number of each type of quenching moiety can be used to increase the total absorptivity within the absorption range. The multi-chromophoric quenchers can be tethered to probes for biomolecules, insoluble supports and/or fluorescent dyes for use in a wide variety of biomolecular assays.

10 Claims, 6 Drawing Sheets

(56) References Cited

OTHER PUBLICATIONS

International Search Report for PCT/US2005/032659, Oct. 1, 2006.
Fang, X., et al, "Single and Multiple Molecular Beacon Probes for DNA Hybridization Studies on a Silica Glass Surface", Proc SPIE Int. Soc. Opt. Eng, Proceedings of SPIE—The International Society for Optical Engineering 1999 Society of Photo-Optical Instrumentation Engineers, Jan. 1999, 149-155, vol. 3602.
May, J. P., et al., "A New Dark Quencher for Use in Genetic Analysis", Chemical Communications, Apr. 21, 2003, 970-971, No. 8.

* cited by examiner

MULTI-CHROMOPHORIC QUENCHER CONSTRUCTS FOR USE IN HIGH SENSITIVITY ENERGY TRANSFER PROBES

1.0 BACKGROUND

1.1 Field

Fluorescence quenchers and methods for using the same are described herein.

1.2 Introduction

Energy transfer (ET) probes are used widely in fluorescence detection of specific target molecules—including DNA, RNA and proteins. ET probes generally consist of a reporter dye labeled analyte specific reagent whose fluorescence signal is quenched by a neighboring quencher chromophore. Typically, the quencher chromophore is covalently linked to the reporter. A change in fluorescence, as a result of a change in quenching, occurs upon interaction with a target. Unfortunately, quenchers available to date tend to have low absorptivity as measured by their extinction coefficients. Often, the extinction coefficients are less than 50,000 and more typically less than 30,000, although some quenchers with higher extinction coefficients are available. A quencher with low absorptivity will have a low quenching capacity of a reporter by Förster energy transfer. In addition, quenchers have a limited range of absorption. Generally, the range of wavelengths that can be absorbed by a quencher is only 150-200 nm wide. Accordingly, there is an ever present need to develop a wider selection of quenchers, as well as quenchers that exhibit higher emission absorbtivity and/or wider ranges of absorption.

2.0 SUMMARY

Dark quencher constructs are described herein that comprise at least two dark quenching moieties, which can be the same or different, linked together by at least one multivalent linking moiety. The phrase "multi-chromophoric quencher," as well as the abbreviation "MCQ," are used interchangeably herein to identify the dark quencher constructs.

The structure of the multi-chromophoric quenchers can be varied to selectively enhance quenching within a specific range of reporter emission wavelengths. This can be accomplished by linking together, into a single molecule, two or more identical quenchers, by reacting the quenchers with a multivalent linker. The resultant MCQ tends to exhibit enhanced absorptivity (absorption cross section) in comparison to its monomeric quencher components. As more and more quenching moieties are added to the structure of the MCQ, the absorptivity within the range of emission wavelengths tends to increase up to a point of diminishing return. Increased absorptivity enhances the Förster type energy transfer between a reporter molecule and a proximate quencher which, in turn, causes significantly lower (quenched) reporter fluorescence. Lower reporter fluorescence increases the sensitivity and the dynamic range of assays which employ the quenchers.

The structure of the multi-chromophoric quencher can also be varied to quench a broad range of reporter emission wavelengths. This can be accomplished by linking together, into a single molecule, two or more different quenchers, by reacting the quenchers with a multivalent linker. The different quenchers can have different absorption ranges and, if so, the resultant MCQ tends to exhibit an increased range of absorption wavelengths in comparison to its monomeric quencher components. As more and more quenching moieties are added, the total absorption range of the MCQ tends to expand, assuming the absorption range of each new quenching moiety is not wholly redundant to the absorption ranges of other quenching moieties on the molecule. MCQs can be designed with a range of absorptions from 200 to at least 750 nm, to quench a large variety of reporters. If the absorption range of each new quenching moiety contains minimal overlap with the absorption range of the other quenching moieties, a broad absorption range is possible using only a few quenching moieties.

The structure of the multi-chromophoric quencher can also be varied to simultaneously broaden the absorption range and increase the total absorption within the absorption range. This can be done by combining the two concepts described above. In other words, multiple types of quenching moieties can be employed to increase the absorption range and a multiple number of each type of quenching moiety can be used to increase the total absorbtivity within the absorption range.

In each multi-chromophoric quencher, quenching moieties can be linked together using at least one multifunctional linker by reacting functional groups on the linker with functional groups on the quenchers. Illustrative reactive functional groups for this purpose, which can be present on the linkers and quenchers, include carboxylic acid, Michael acceptors, Michael donors, aromatic esters of carboxylic acid, hydroxysuccinimide esters, hydroxybenzotriazole esters, acid halides, acyl imidazoles, thioesters, nitrophenyl esters, hydroxyl, haloalkyls, dienophile groups, aldehydes, ketones, sulfonyl halide groups, thiol groups, amine groups, sulfhydryl groups, cyanuryl halide, epoxides, phosphoramidites, substituted hydrazines, and substituted diazyl alkanes.

The multi-chromophoric quenchers can be formed using any type of linker that is capable of reacting with multiple activated quencher molecules to form a linkage. For example, the linker can be selected from multi-functional monomers, branched or linear polymers and dendrimers. The nature of the multivalent linking moieties formed can vary widely, and can comprise any monomeric, linear polymeric, branched polymeric, or dendritic backbones.

The quenching moieties in the multi-chromophoric quenchers can be pendent from a single multivalent linking moiety. This is the case, for example, when the quenching moieties are attached to a single monomeric, polymeric or dendritic backbone. Alternatively, each quenching moiety can be separated by a linking moiety in linear fashion within a polymeric backbone.

The multi-chromophoric quenchers additionally comprise one or more free reactive functional groups to facilitate attachment to additional substances. Illustrative additional substances include insoluble supports, probes for biomolecules, fluorescent dyes, and combinations thereof. These reactive functional groups can be present anywhere on the MCQ. The reactive group or groups can be pendant from the multivalent linker moiety or any one of the quencher moieties, but are more typically present on the multi-valent linking moiety. Useful reactive functional groups include, for example: (a) carboxyl groups and various derivatives thereof; (b) hydroxyl groups; (c) haloalkyl groups; (d) dienophile groups; (e) aldehyde or ketone groups; (f) sulfonyl halide groups; (g) thiol groups; (h) amine groups; (i) Michael donors and Michael acceptors; (j) epoxides; (k) cyanuryl halide; (l) phosphoramidites, (m) substituted hydrazines, (n) substituted diazyl alkanes, and (o) other standard functional groups in nucleic acid synthesis.

The multi-chromophoric quenchers can be linked to other substances through an attachment formed by reacting a reactive functional group on the MCQ with a reactive group on the other substance. The conjugate formed comprises a carrier portion and at least one quenching portion, where each quenching portion comprises at least two dark quenching moieties, which can be the same or different, linked together by at least one multivalent linker moiety. Suitable carrier portions include moieties that comprise one or more insoluble supports, one or more probes for biomolecules, one or more fluorescent dyes, and combinations thereof.

The multi-chromophoric quenchers can be used to optimize the performance of ET probes. Novel dark quencher constructs can be designed to quench all fluorescent emissions with equal efficiency, eliminating costs associated with supplying multiple quencher products.

These and other features of the present invention are set forth herein.

3.0 BRIEF DESCRIPTION OF THE DRAWINGS

The skilled artisan will understand that the drawings, described below, are for illustration purposes only. The drawings are not intended to limit the scope of the present teachings in any way.

Figure 1:
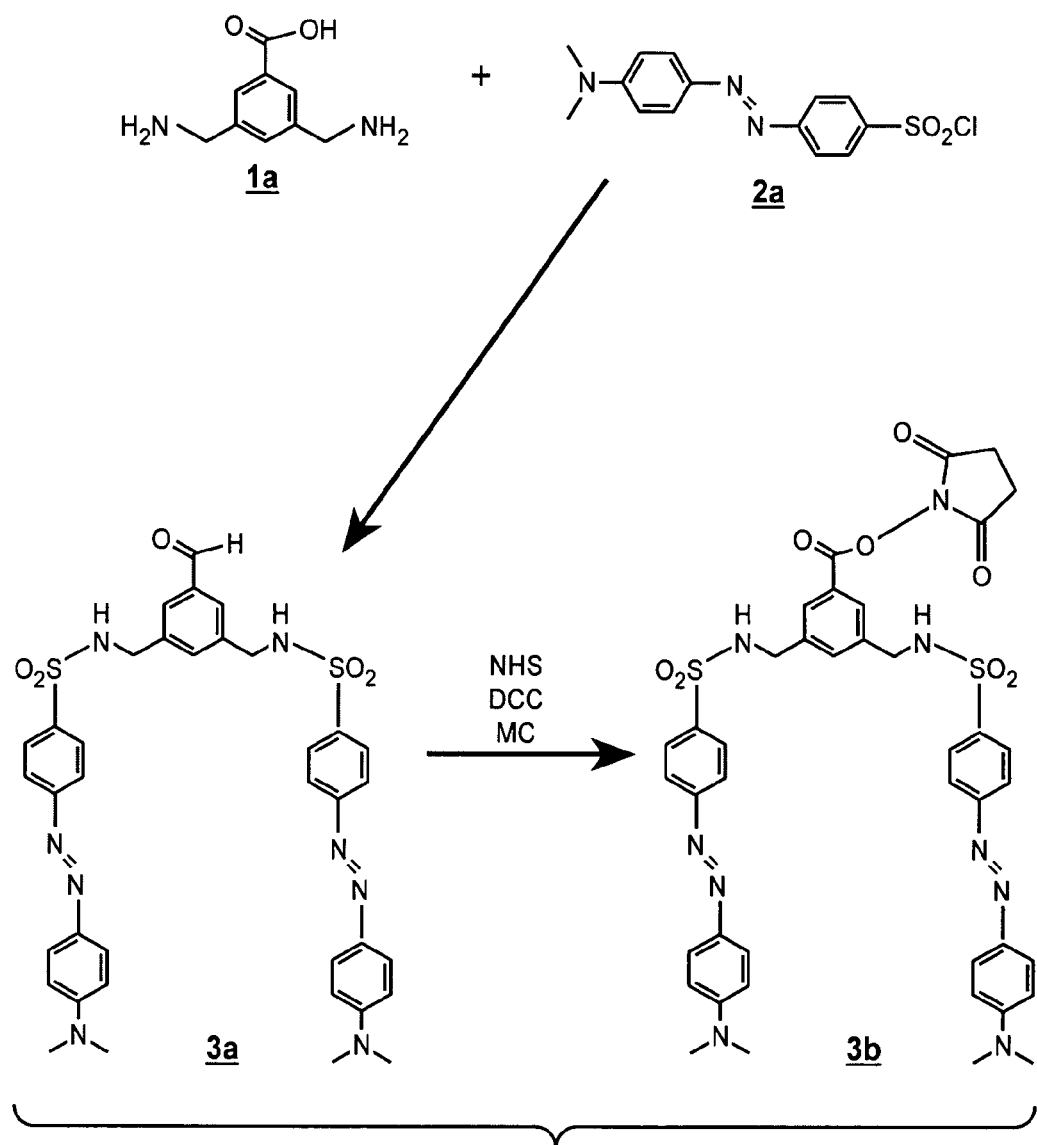
FIG. 1 shows a method of linking two identical chromophores to form an illustrative multi-chromophoric quencher.

4.0 DESCRIPTION OF THE VARIOUS EMBODIMENTS 4.1 Definitions

Unless defined otherwise, all technical and scientific terms used herein have the meaning commonly understood by those of ordinary skill in the art. The following words and phrases have the following meanings:

"Quenching" refers to a decrease in the fluorescence of a specified fluorescent reporter caused by a quencher by energy transfer, regardless of the mechanism.

"Dark quencher" and "dark quenching moiety" refer to a compound and moiety, respectively, that exhibits an extinction coefficient of at least 5,000, a quantum yield no greater than 0.05, and an absorption maximum greater than 300 nm.

"Multi-chromophoric quencher" and the abbreviation "MCQ" are used herein, interchangeably, to identify a dark quencher construct containing multiple dark quenching moieties connecting by one or more multivalent linking moieties.

"Energy transfer" refers to the process by which the excited state energy of an excited group, e.g., on a fluorescent reporter dye, is conveyed through space or through bonds to another group, e.g., a quencher moiety, which can attenuate (quench) or otherwise dissipate or transfer the energy. Energy transfer can occur through fluorescence resonance energy transfer, direct energy transfer, and other mechanisms. The exact energy transfer mechanisms is not critical. Therefore, any reference to energy transfer herein encompasses all of these mechanistically-distinct phenomena.

"Energy transfer pair" refers to any two moieties that participate in energy transfer. Typically, one of the moieties acts as a fluorescent reporter, i.e., donor, and the other acts as a fluorescence quencher, i.e., acceptor. See *Fluorescence resonance energy transfer*, Selvin P. (1995); *Methods Enzymol*, 246:300-334; dos Remedios C. G., J. *Struct. Biol.* 115:175-185 (1995); *Resonance energy transfer: methods and applications*, Wu P. and Brand L., Anal Biochem 218:1-13 (1994).

For example, one type of energy transfer, fluorescence resonance energy transfer (FRET), is a distance-dependent interaction between two moieties in which excitation energy, i.e., light, is transferred from a donor ("reporter") to an acceptor without transmission of a photon. The acceptor can be fluorescent and emit the transferred energy at a longer wavelength, or it can be non-fluorescent and serve to diminish the detectable fluorescence of the reporter (quenching). FRET can be either an intermolecular or intramolecular event, and is dependent on the inverse sixth power of the separation of the donor and acceptor, making it useful over distances comparable with the dimensions of biological macromolecules. Thus, the spectral properties of the energy transfer pair as a whole change in some measurable way if the distance between the moieties is altered by some critical amount. Self-quenching probes incorporating fluorescent donor-non-fluorescent acceptor combinations have been developed primarily for detection of proteolysis (see Matayoshi, Science 247:954-958 (1990)) and nucleic acid hybridization (see *Detection of Energy Transfer and Fluorescence Quenching*, Morrison, L., Nonisotopic DNA Probe Techniques, L. Kricka, Ed., Academic Press, San Diego, pp 311-352 (1992); Tyagi S., Nat. Biotechnol., 16:49-53 (1998); Tyagi S., Nat. Biotechnol 14:303-308 (1996)). In most applications, the donor and acceptor dyes are different, in which case FRET can be detected by the appearance of sensitized fluorescence of the acceptor or by quenching of donor fluorescence.

"Linking moiety" refers to a chemical moiety comprising a one or more atoms that covalently attaches one moiety or molecule to another, e.g., a quencher to a polynucleotide. A "cleavable linking moiety" is a linking moiety which has one or more covalent bonds which can be broken by a reaction or condition. For example, an ester in a molecule is a linking moiety that can be cleaved by a reagent, e.g., sodium hydroxide, resulting in a carboxylate-containing fragment and a hydroxyl-containing product.

"Reactive functional group" is a chemically reactive substituent or moiety, e.g., a nucleophile or electrophile, on a molecule which is capable of reacting with another molecule to form a covalent bond. Reactive functional groups include active esters, which are commonly used for coupling with amine groups. For example, N-hydroxysuccinimide (NHS) esters have selectivity toward aliphatic amines to form aliphatic amide products which are very stable. Their reaction rate with aromatic amines, alcohols, phenols (tyrosine), and histidine is relatively low. Reaction of NHS esters with amines under nonaqueous conditions is facile, so they are useful for derivatization of small peptides and other low molecular weight biomolecules. Virtually any molecule that contains a carboxylic acid or that can be chemically modified to contain a carboxylic acid can be converted into its NHS ester. NHS esters are available with sulfonate groups that have improved water solubility.

"Linker" is a molecule that contains multiple reactive functional groups.

"Monomer" or "monomeric," as used herein, refers generally to any non-polymeric chemical compound, regardless of whether it can be reacted, in series, to form units in a polymer.

"Polymer" and "polymeric" means any molecule, built from one or more types of monomers, that consists of multiple repeating chemical units formed by joining the monomers together in a chain. For the purposes herein, the term polymer embraces dimers, trimers, tetramers and oligomers.

"Dendrimers" and "dendritic" means any polymer that has an ordered tree-like or star-like structure built from monomers added in steps, often with intermediate protection and deprotection steps.

"Insoluble support" refers to any material that is not soluble in the media containing the sample to be analyzed, including but not limited to semi-solid and solid materials, and especially including materials upon which a nucleic acid or polypeptide can be synthesized, attached or otherwise immobilized. Suitable insoluble supports include cell surfaces, cellulose, dextran, liposomes, lipid bilayers, self assembling monolayers such as Langmuir-Blodgetee, micelles and latexes, organic polymers, copolymers and graft copolymers comprising units formed from olefin monomers, styrene, (meth)acrylates, hydroxyalkyl(meth)acrylates, acrylamide, and mixtures thereof, and inorganic materials such as glass, silica, controlled-pore-glass (CPG), and reverse-phase silica. The configuration of a solid insoluble support can take any form including particles, magnetic or nonmagnetic beads, membranes, frits, fibers, tubes, capillaries, slides, plates, micromachined chips, porous or non-porous surfaces, addressable arrays, and polynucleotide-immobilizing mediums.

"Biomolecule" means any amino acid, polypeptide, nucleoside, nucleotide, polynucleotide, carbohydrate, vitamin, hormone, and any other compound that can be produced by an organism.

"Probe for a biomolecule" is any chemical species or group that reacts, attaches, hybridizes, changes conformation, or otherwise interacts with and/or is affected by, one or more biomolecules, when said biomolecules are proximate to the probe, in a manner that can be detected. Probes for biomolecules can comprise, and usually do comprise, other biomolecules and/or analogs thereof. For example, a probe for a DNA sequence includes a complimentary DNA sequence or complementary peptide nucleic acid sequence. Similarly a probe for an analyte might comprise an enzyme specific to the analyte and visa versa. Additionally, a probe for an antigen might comprise an antibody specific to the antigen and visa versa. A wide variety of mechanisms can be used to signal when a probe for a biomolecule interacts and/or is affected by a proximate biomolecule, including, but not limited to, quenching or unquenching of a proximate fluorescent dye.

"Amino acid" refers to naturally occurring and synthetic amino acids, as well as amino acid analogs and amino acid mimetics that function in a similar manner.

"Polypeptide or "Peptide," as used interchangeably herein, refers to a polymer including proteins, synthetic peptides, antibodies, peptide analogs, and peptidomimetics in which the monomers are amino acids joined together through amide bonds. When the amino acids are .alpha.-amino acids, either the L-optical isomer or the D-optical isomer can be used. Additionally, unnatural amino acids, for example, valanine, phenylglycine and homoarginine are also included. Commonly encountered amino acids that are not gene-encoded can also be used. All of the amino acids used can be either the D- or L-optical isomer. In addition, other peptidomimetics are also useful. For a general review, see Spatola, A. F., in Chemistry and Biochemistry of Amino Acids, Peptides and Proteins, B. Weinstein, eds., Marcel Dekker, New York, p. 267 (1983).

"Polynucleotide" and "oligonucleotide" are used interchangeably and mean single-stranded and double-stranded polymers of nucleotide monomers, including 2'-deoxyribonucleotides (DNA) and ribonucleotides (RNA) linked by internucleotide phosphodiester bond linkages, or internucleotide analogs, and associated counter ions, e.g., H.sup.+, NH.sub.4.sup.+, trialkylammonium, $Mg^{2+}$, $Na^+$ and the like. A polynucleotide can be composed entirely of deoxyribonucleotides, entirely of ribonucleotides, or chimeric mixtures thereof. Polynucleotides can be comprised of nucleobase and sugar analogs. Polynucleotides typically range in size from a few monomeric units, e.g., 5-40 when they are more commonly frequently referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytidine, "G" denotes deoxyguanosine, and "T" denotes thymidine, unless otherwise noted.

"Internucleotide analog" means a phosphate ester analog or a non-phosphate analog of a polynucleotide. Phosphate ester analogs include: (i) C.sub.1-C.sub.4 alkylphosphonate, e.g. methylphosphonate; (ii) phosphoramidate; (iii) C.sub.1-C.sub.6 alkyl-phosphotriester, (iv) phosphorothioate; and (v) phosphorodithioate. Non-phosphate analogs include compounds wherein the sugar/phosphate moieties are replaced by an amide linkage, such as a 2-aminoethylglycine unit, commonly referred to as PNA See, e.g., WO 92/20702 and Nielsen, Science 254: 1497-1500 (1991).

"Analyte" means any compound or molecule of interest for which a diagnostic test is performed. An analyte can be, for example, a nucleic acid, protein, peptide, carbohydrate, polysaccharide, glycoprotein, hormone, receptor, antigen, antibody, virus, metabolite, cofactor, inhibitor, drug, nutrient, growth factor, etc., without limitation.

"Substituted" as used herein refers to a molecule wherein one or more hydrogen atoms are replaced with one or more non-hydrogen atoms, functional groups or moieties. For example, an unsubstituted nitrogen is —$NH_2$, while a substituted nitrogen is —$NHCH_3$. Exemplary substituents include but are not limited to halo, e.g., fluorine and chlorine, $C_1$-$C_8$ alkyl, sulfate, sulfonate, sulfone, amino, ammonium, amido, nitrile, nitro, alkoxy (—OR where R is $C_1$-$C_{12}$ alkyl), phenoxy, aromatic, phenyl, polycyclic aromatic, heterocycle, water-solubilizing group, and lining moiety.

4.2 Multi-Chromophoric Linkers Generally

The structure of the multi-chromophoric quenchers can be varied to selectively enhance quenching within a specific range of reporter emission wavelengths. This can be accomplished by linking together, into a single molecule, two or more identical quenchers, by reacting the quenchers with a multivalent linker. The resultant MCQ tends to exhibit enhanced absorptivity (absorption cross section) in comparison to its monomeric quencher components. As more and more quenching moieties are added to the structure of the MCQ, the absorptivity within the range of emission wavelengths tends to increase up to a point of diminishing returns. For example, some MCQs exhibit an absorptivity that is more than double the absorptivity of their individual quencher components. Increased absorptivity can enhance the Förster type energy transfer between a reporter molecule and a proximate quencher which, in turn, can cause significantly lower (quenched) reporter fluorescence. Lower reporter fluorescence increases the sensitivity and the dynamic range of assays which employ the quenchers.

This concept is visually illustrated in FIGS. 1, 3, 5A and 6.

FIG. 1 diagrams the reaction of one equivalent of 3,5-dimethamino benzoic acid linker 1a with two or more equivalents of Dabsyl chloride quencher 2a to form an acid functional MCQ 3a. The acid functional MCQ 3a can be converted to an NHS ester functional MCQ 3b.

Figure 3:
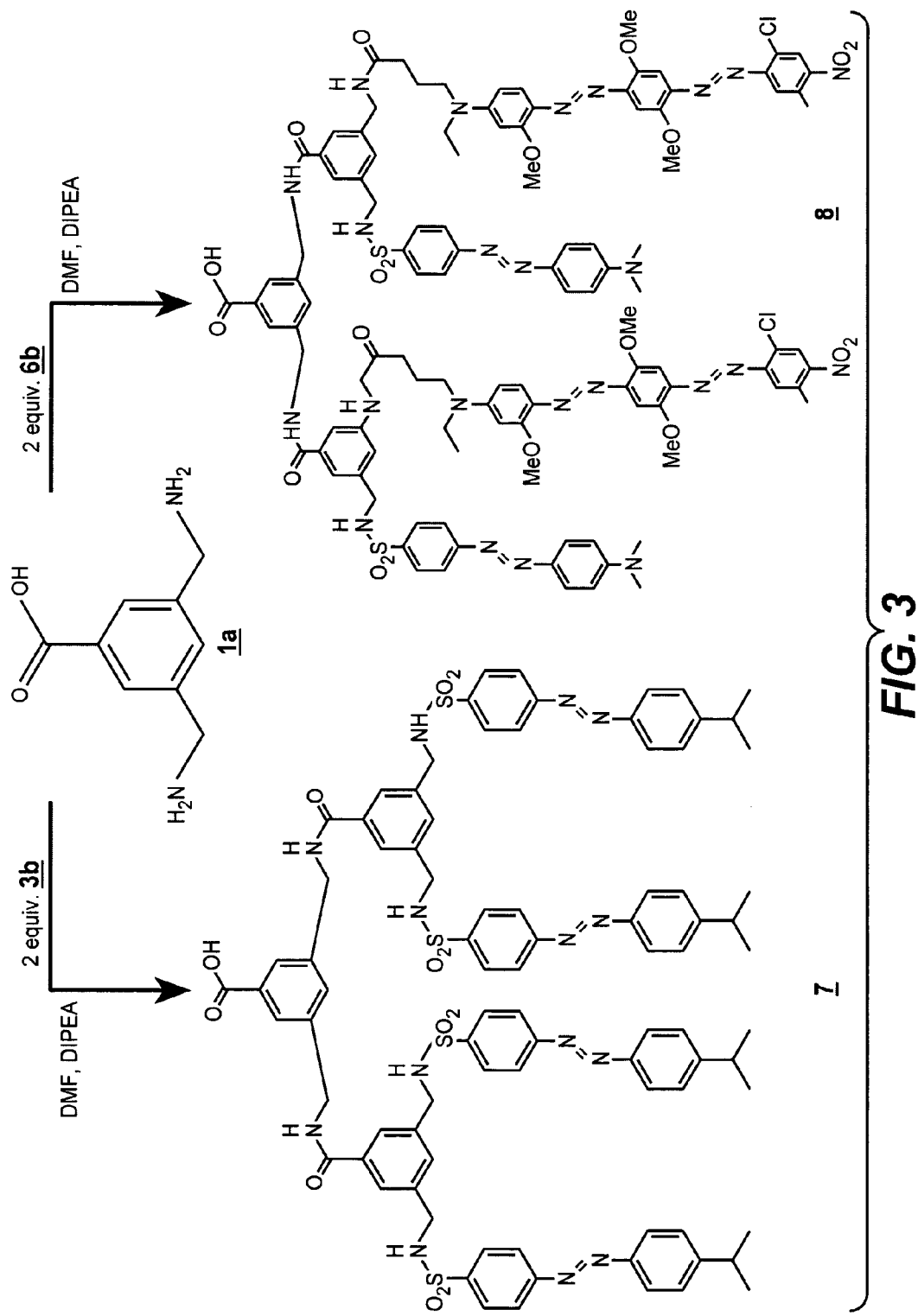
FIG. 3 shows a method of linking a total of four chromophores, whether identical or a mixture of two types, to form a branched tetra-chromophoric quencher.

FIG. 3 shows two reaction paths. In the first reaction path one equivalent of 3,5-dimethamino benzoic acid linker 1a is reacted with two or more equivalents of the NHS ester functional MCQ 3b from FIG. 1. The product, MCQ 7, has four identical quencher moieties.

Figure 5A:
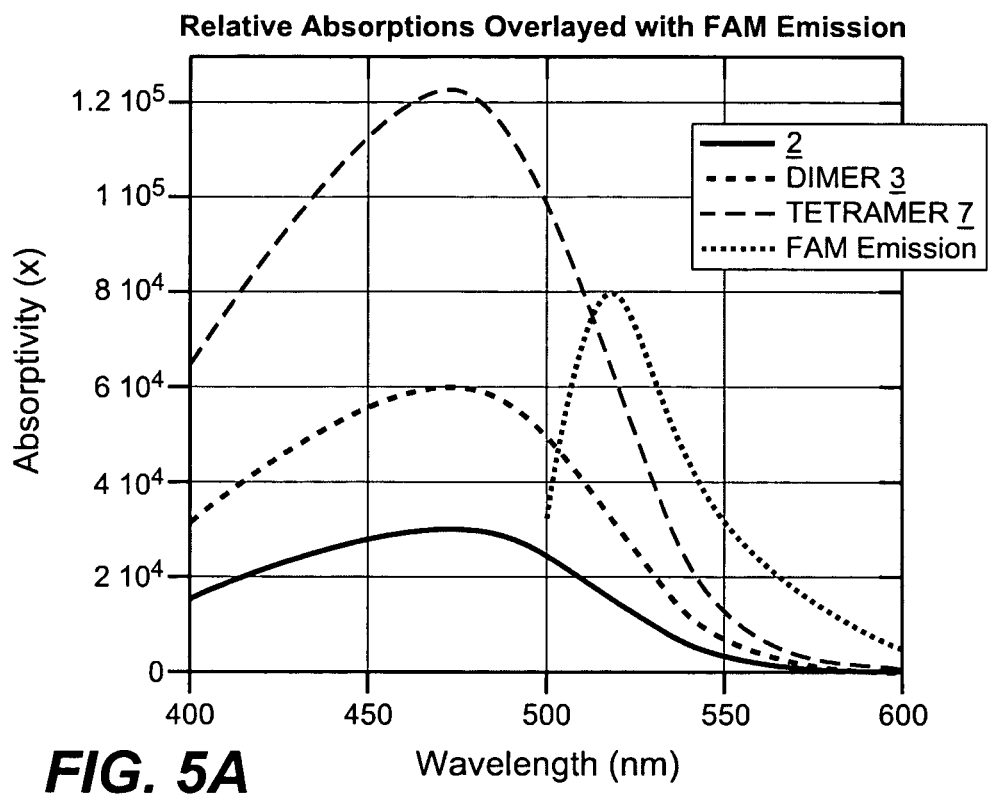
FIG. 5A is a graph of the expected increase in absorptivity when comparing a monomeric quencher to a bis-chromophoric quencher and when comparing a bis-chromophoric quencher to a tetra-chromophoric quencher.

FIG. 5A is a graph that compares the absorptivity of a Dabsyl chloride 2a with the absorptivity of MCQs 3a and 7 over wavelengths ranging from 400 to 600 nm. In general, as evident from the graph, the more quencher moieties that are present, the higher the absorptivity. Accordingly, MCQ 7 shows greater absorptivity than MCQ 3 and, in turn, MCQ 3 shows greater absorptivity than the Dabsyl quencher 2a. As an additional frame of reference, the emission spectra of a common reporter dye, FAM, is also shown.

Figure 6:
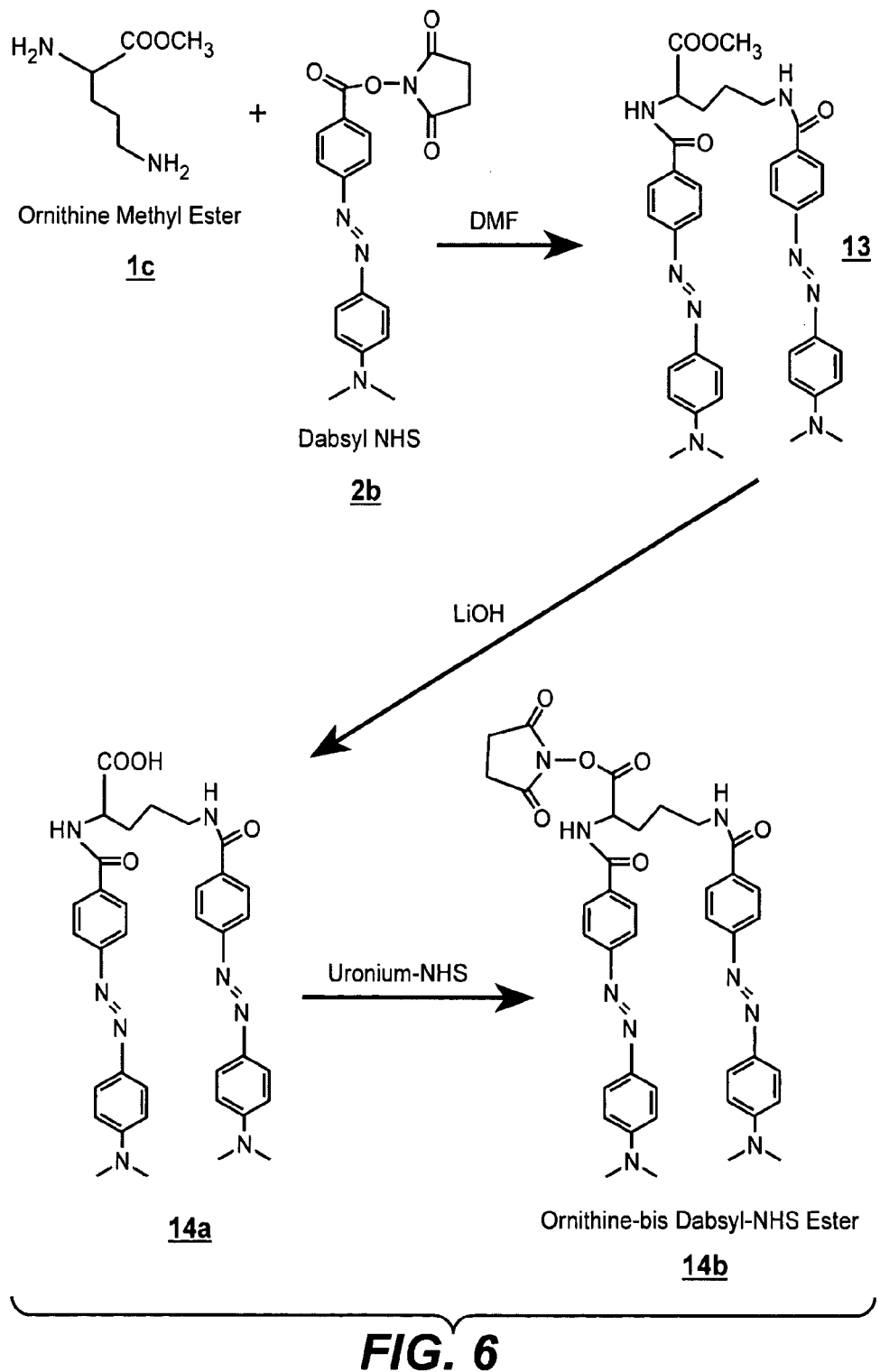
FIG. 6 shows a method of linking two identical chromophores to form an illustrative multi-chromophoric quencher.

FIG. 6 diagrams the reaction of one equivalent of ornithine methyl ester 1c with Dabsyl NHS ester quencher 2b to form a methylester functional MCQ 13. The methylester functional MCQ 13 can be further converted into an acid functional MCQ 14a by reaction with lithium hydroxide. In turn the acid functional MCQ 14a can be converted to an NHS ester functional MCQ 14b by reaction with uranium-NHS.

The structure of the multi-chromophoric quencher can also be varied to quench a broader range of reporter dye emission wavelengths than previously possible. This can be accomplished by linking together, into a single molecule, two or more different quenchers, by reacting the quenchers with a multivalent linker. The different quenchers can have different absorption ranges. The resultant MCQ tends to exhibit an increased range of absorption wavelengths in comparison to its monomeric quencher components. As more and more quenching moieties are added, the total absorption range of the MCQ tends to expand, assuming the absorption range of each new quenching moiety is not wholly redundant to the ranges provided by the other quenching moieties. For example, MCQs can be designed with a range of absorptions from 200 to at least 750 nm, to quench a large variety of reporters. If the absorption range of each new quenching moiety contains minimal overlap with the absorption range of the other quenching moieties, a broad absorption range can be obtained with only a few quenching moieties. This concept is visually illustrated in FIGS. 2, 3 and 5B.

Figure 2:
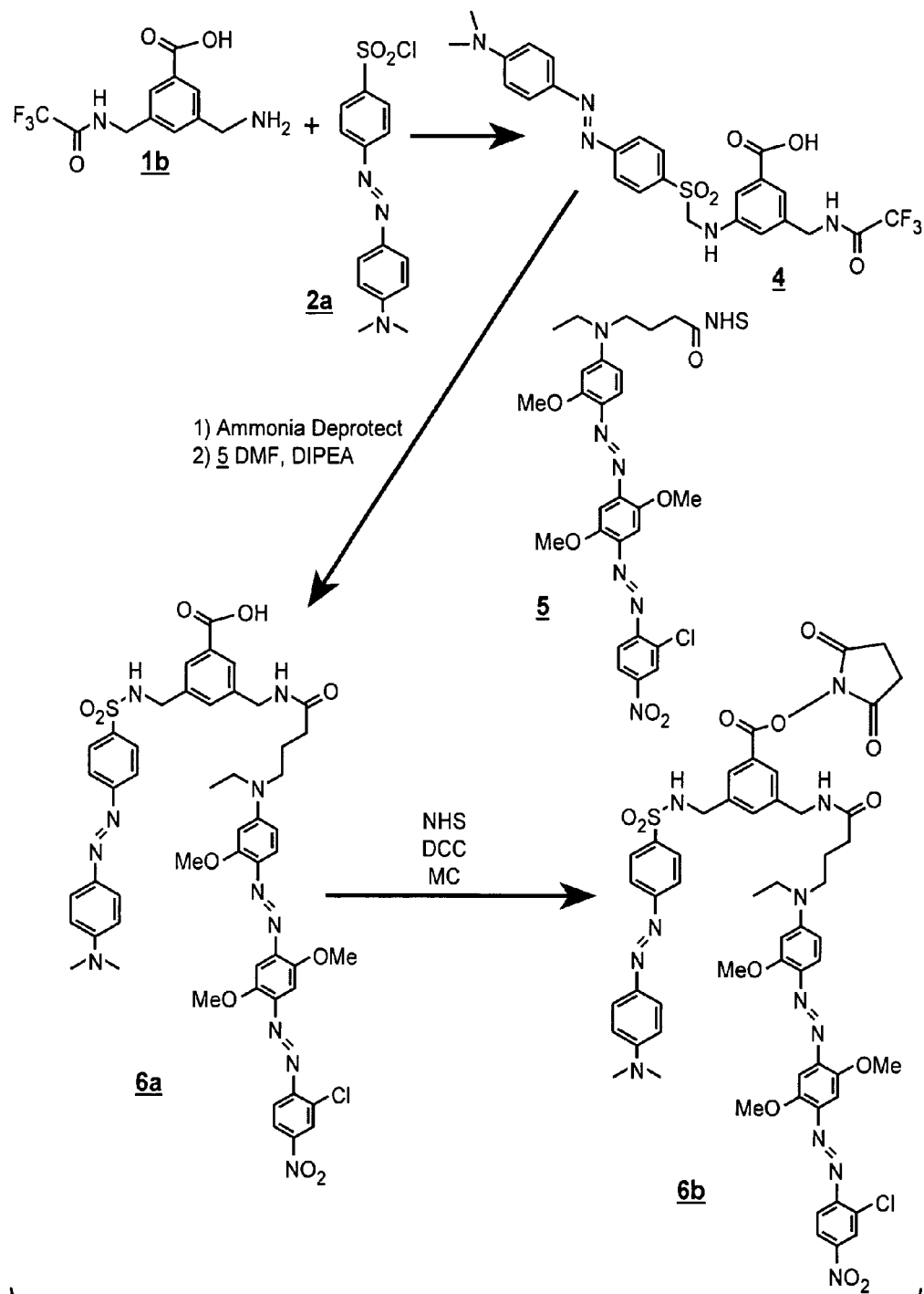
FIG. 2 shows a method of linking two different chromophores to form an illustrative multi-chromophoric quencher.

FIG. 2 shows the reaction between one equivalent of Dabsyl chloride 2a and one equivalent of a partially protected 3,5-dimethaimino benzoic acid 1b. The product, intermediate 4, is ammonia deprotected and reacted with at least one equivalent of the NHS ester of Biosearch Technologies, Inc.'s Black Hole Quencher 1 (BHQ-1) 5. The final product is an acid functional MCQ 6 that contains two different quenching moieties. The acid functional MCQ 6 can be converted to an NHS ester functional MCQ 6b.

FIG. 3 shows two reaction paths. In the second reaction path one equivalent of 3,5-dimethamino benzoic acid linker 1a is reacted with at least two or more equivalents of the NHS ester functional MCQ 6b from FIG. 1. The product, MCQ 7, has two types of quencher moieties.

Figure 5B:
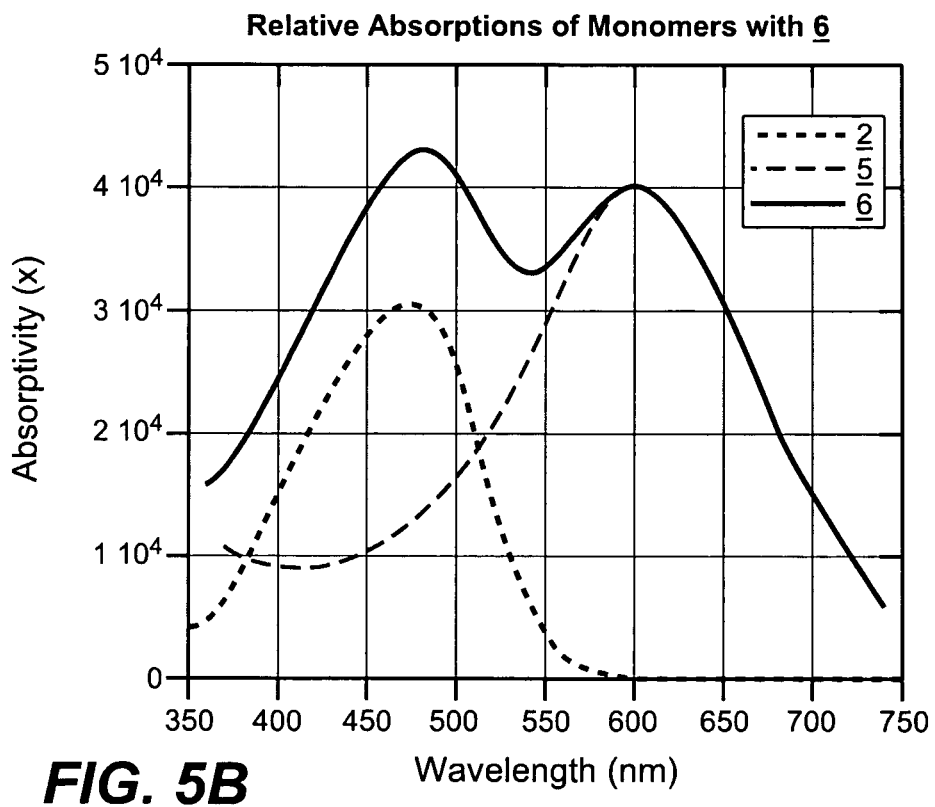
FIG. 5B is a graph of the expected broadening in the absorption range for the hetero tetra-chromophoric quencher of FIG. 2 in comparison to the absorption range for the monomeric chromophores used therein.

FIG. 5B is a graph that compares the predicted absorptivity of Dabsyl chloride 2a, BHQ-1 quencher 5 and MCQ 6a. As evident from FIG. 5B, MCQ 6a has an absorptivity range that is greater than, and is roughly the summation of, the absorptivity ranges of Dabsyl quencher 2a and BHQ-1 quencher 5.

The structure of the multi-chromophoric quencher can also be varied to simultaneously broaden the absorption range and increase the total absorption within the absorption range. This can be done by combining the two concepts described above. In other words, multiple types of quenching moieties can be employed to increase the absorption range and a multiple number of each type of quenching moiety can be used to increase the total absorptivity within the absorption range.

4.3 Quencher Moieties

Dark quenchers that can be reacted to form dark quencher moieties in the multi-chromophoric quenchers described herein are not limited—as long as the dark quenchers contain, or can be modified to contain, a reactive functional group that permits linkage to another molecule. Suitable dark quenchers include any commercially available dark quencher. Table 1 below provides a non-limiting list of suitable commercially available dark quenchers along with a general description of their properties:

TABLE 1

SUITABLE DARK QUENCHERS

| Dark Quencher | Range | Absorption Max. | Extinction Coeff. |
|---|---|---|---|
| LQ2 | 500-700 | ND | ~10,000 |
| Iowa Black | 520-710 | 606, 651 | ~10,000 |
| Dabcyl | 350-550 | 453 | 32,000 |
| Dabsyl | 360-560 | 466 | 33,000 |
| QSY 7 | 500-610 | 560 | 92,000 |
| QSY 9 | 500-610 | 562 | 86,000 |
| QSY 21 | 550-720 | 660 | 89,000 |
| QSY 35 | 390-530 | 472 | 23,000 |
| Epoch | 420-620 | 522 | 34,000 |
| BHQ-1 | 488-556 | 538 | 50,000 |
| BHQ-2 | 550-645 | 584 | 57,600 |
| Methyl Red | 300-520 | 437 | 21,000 |
| 4,5' dimethoxy-6-carboxyfluoroscein | 480-530 | 512 | 78,200 |

All the dark quencher moieties can be the same. Alternatively, some of the dark quencher moieties can be different. As set forth in the preceding section, this permits increases in absorptivity and absorption range, respectively.

Illustrative dark quencher moieties include, but are not limited to, the following: diazoaryl; bisdiazoaryl; aminanthraquinone; bis-n-phenyl-rhodamine; 4-5 dihydroxyfluorescein; and 4,5-dialkoxyfluorescein. More particularly, at least one or all of the dark quenching moieties can be selected from the following:

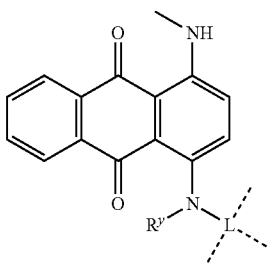

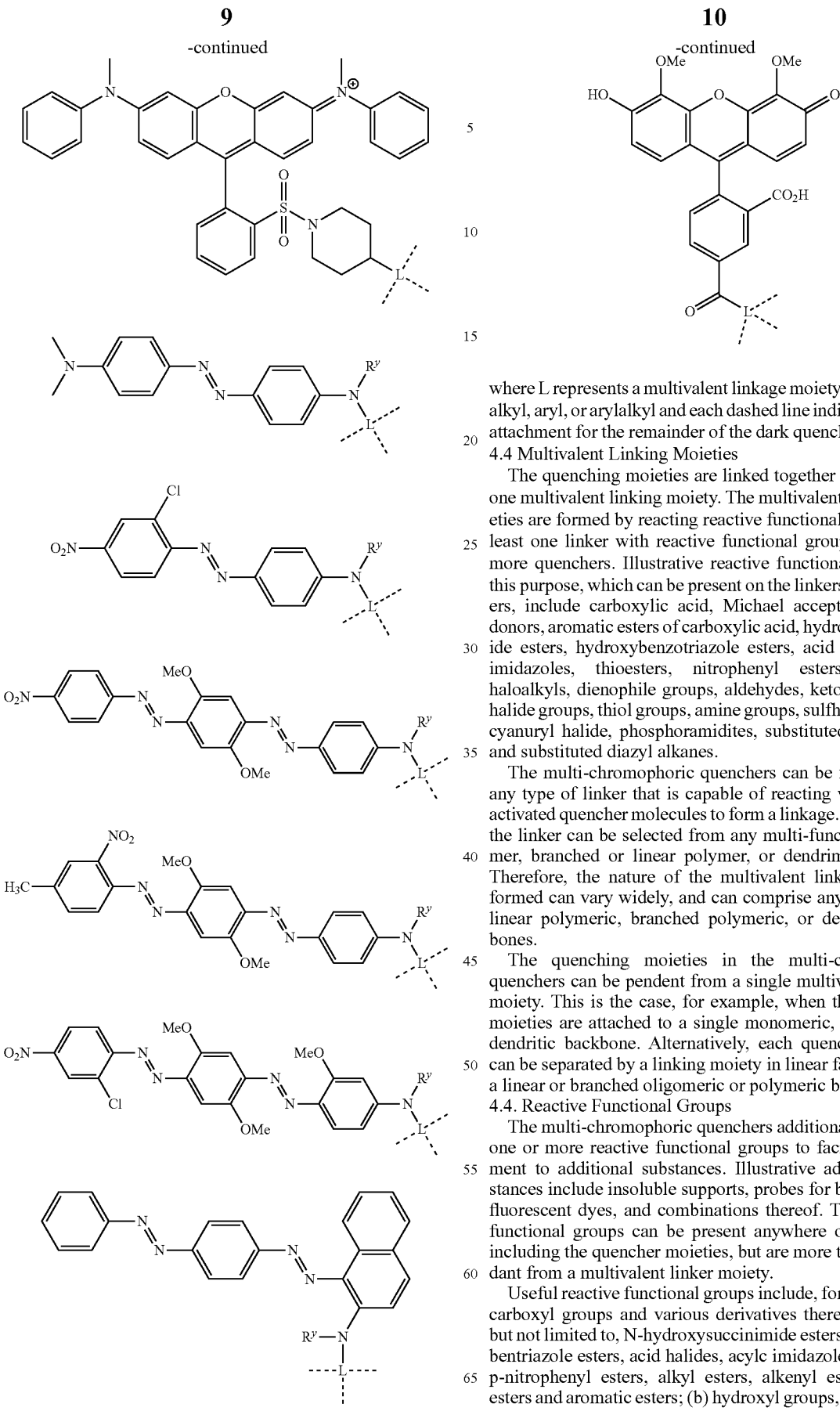

where L represents a multivalent linkage moiety, $R^y$ is H, $C_{1-4}$ alkyl, aryl, or arylalkyl and each dashed line indicates point of attachment for the remainder of the dark quencher construct.

4.4 Multivalent Linking Moieties

The quenching moieties are linked together using at least one multivalent linking moiety. The multivalent linking moieties are formed by reacting reactive functional groups on at least one linker with reactive functional groups on two or more quenchers. Illustrative reactive functional groups for this purpose, which can be present on the linkers and quenchers, include carboxylic acid, Michael acceptors, Michael donors, aromatic esters of carboxylic acid, hydroxysuccinimide esters, hydroxybenzotriazole esters, acid halides, acyl imidazoles, thioesters, nitrophenyl esters, hydroxyl, haloalkyls, dienophile groups, aldehydes, ketones, sulfonyl halide groups, thiol groups, amine groups, sulfhydryl groups, cyanuryl halide, phosphoramidites, substituted hydrazines, and substituted diazyl alkanes.

The multi-chromophoric quenchers can be formed using any type of linker that is capable of reacting with multiple activated quencher molecules to form a linkage. For example, the linker can be selected from any multi-functional monomer, branched or linear polymer, or dendrimer structure. Therefore, the nature of the multivalent linking moieties formed can vary widely, and can comprise any monomeric, linear polymeric, branched polymeric, or dendritic backbones.

The quenching moieties in the multi-chromophoric quenchers can be pendent from a single multivalent linking moiety. This is the case, for example, when the quenching moieties are attached to a single monomeric, polymeric or dendritic backbone. Alternatively, each quenching moiety can be separated by a linking moiety in linear fashion within a linear or branched oligomeric or polymeric backbone.

4.4. Reactive Functional Groups

The multi-chromophoric quenchers additionally comprise one or more reactive functional groups to facilitate attachment to additional substances. Illustrative additional substances include insoluble supports, probes for biomolecules, fluorescent dyes, and combinations thereof. These reactive functional groups can be present anywhere on the MCQ, including the quencher moieties, but are more typically pendant from a multivalent linker moiety.

Useful reactive functional groups include, for example: (a) carboxyl groups and various derivatives thereof including, but not limited to, N-hydroxysuccinimide esters, N-hydroxybentriazole esters, acid halides, acylc imidazoles, thioesters, p-nitrophenyl esters, alkyl esters, alkenyl esters, alkynyl esters and aromatic esters; (b) hydroxyl groups, which can be converted to esters, ethers, aldehydes, etc.; (c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups, which are capable of participating in Diels-Alder reactions such as, for example, maleimido groups; (e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, sulfonamides; (g) thiol groups, which can be, for example, converted to disulfides or reacted with acyl halides; (h) amine groups, which can be, for example, be acylated, alkylated or oxidized; (i) Michael donors and Michael acceptors such as, for example, alkenes, (j) epoxides, which can react with, for example, amines and hydroxyl compounds, (k) cyanuryl halide; (l) phosphoramidites; (m) substituted hydrazines; (n) substituted diazyl alkanes; and (o) other standard functional groups in nucleic acid synthesis.

The reactive functional groups can be chosen so that they do not participate in, or interfere with, the reactions necessary to assemble the MCQ. Alternatively, a reactive functional group can be protected from participating in the reaction by the presence of a protecting group. Those skilled in the art understand how to protect a particular reactive functional group such that it does not interfere with a chosen set of reaction conditions. See, for example, Protective Groups In Organic Synthesis, Green et al., John Wiley & Sons, New York (1991).

Figure 4:
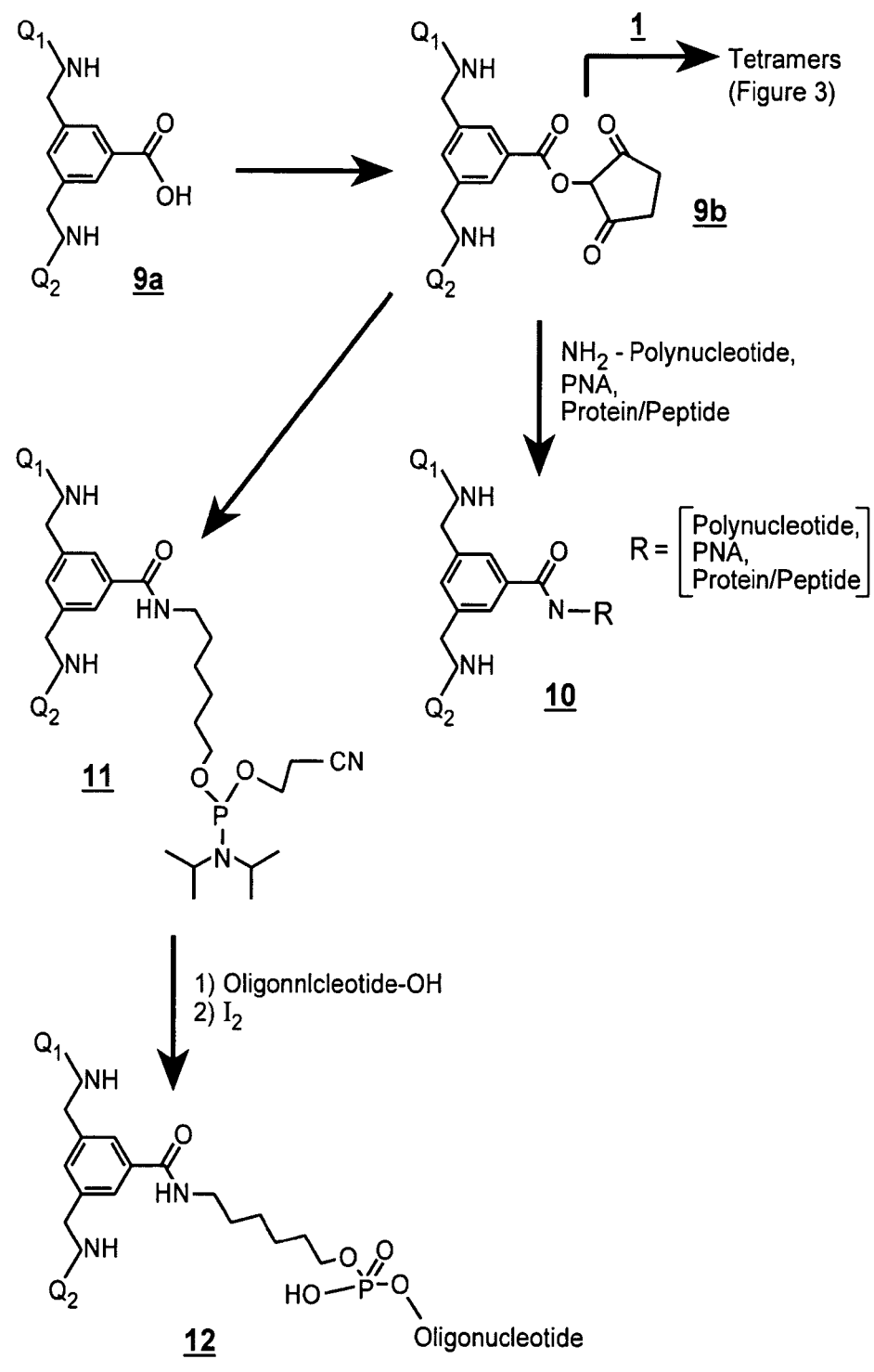
FIG. 4 shows various methods by which a multi-chromophoric quencher can be employed as a single activatable unit, i.e., NHS ester, phosphoramidite, or insoluble support to label ET probes.

This concept is illustrated by FIGS. 1-4 and 6. In FIGS. 1-4 and 6, various carboxylic acid functional MCQs are illustrated (structures 3a, 6a, 7, 8, 9a and 14a). As shown by 3b, 6b, 9b and 14b, the carboxylic acid groups on these structures can be activated to from NHS ester groups. In addition, as shown in FIG. 4, the NHS ester functional MCQ 9b can be further reacted to form a phosphoramidite functional MCQ 11.

4.5 Monomeric MCQs

The multi-chromophoric quenchers can be formed by reacting a monomeric linker that is capable of reacting with activated quencher molecules to form linkages. Suitable monomeric linkers have two or more reactive functional groups which can be, for example, be any of the reactive functional groups described in section 4.4. However, if at least three reactive functional groups exist, then one reactive functional group can remain free to form future linkages to other substances (e.g., insoluble supports, probes for biomolecules, fluorescent dyes, etc. . . . )

Accordingly, the MCQ can comprise the following formula:

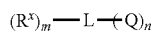

where m is a whole number greater than or equal to 1; where n is a whole number greater than or equal to 2 and generally ranging from 2 to 8; where each Q is a dark quenching moiety that can be the same or different; where L is a multivalent linking moiety comprising the reacted residue of a multifunctional monomer (generally comprising less than 50 atoms); and where each $R^x$ is a reactive functional group that can be the same or different. More particularly, m is 1, n is a number ranging from 2 to 8, and L is selected from linking moieties that have from 1-20 non-hydrogen atoms selected from the group consisting of C, N, O, S, Si and P. More particularly, L comprises one or more ester, urea, urethane, carbonate, carbamate, amide, carboxamide, amine, phosphate, sulfonamide, ether, thioether, carbazide, hydrazine, silane, and siloxane linkages.

The linkers can be multi-functional cyclic or aryl monomers. Suitable multi-functional aryl monomers include, for example, multifunctional benzoic acids such as 3,5-dimethamino benzoic acid. Accordingly, the MCQ can comprise the following structure:

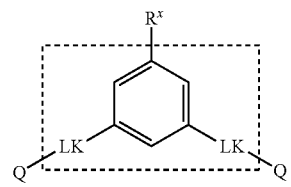

where each Q is a dark quencher that can be the same or different; where $R^x$ is a reactive functional group; and where the remainder of the molecule (contained within the dashed line box) is a multivalent linking moiety wherein each LK, independently, is a moiety that comprises one or more ester, urea, urethane, carbamate, amide, amine, phosphate, sulfonamide, ether, thioether, carbazide, hydrazone, silane, and siloxane linkages. Illustrative linkers which can be used to make such MCQs include, but are not limited to, the following:

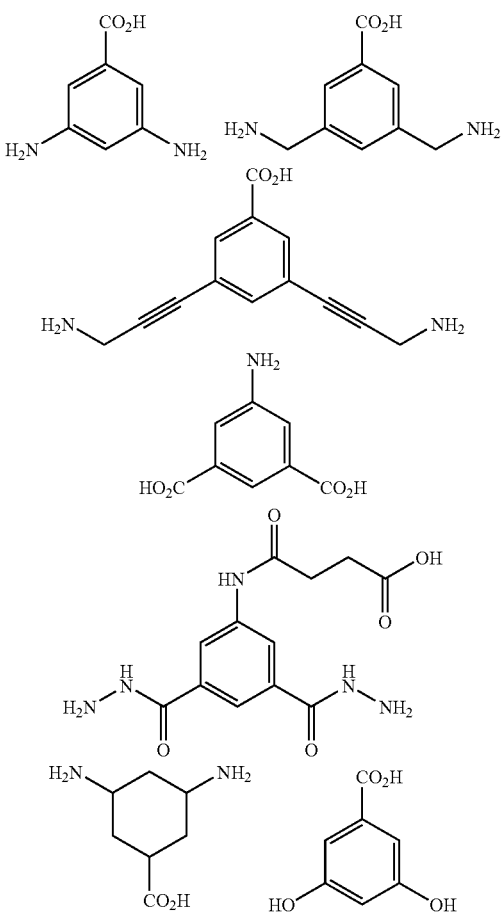

FIGS. 1 and 2 are illustrative.

In FIG. 1, a 3,5-dimethamino benzoic acid linker 1a is reacted with a Dabsyl chloride quencher 2a in a 2:1 or higher ratio to form MCQ 3a. The MCQ 3a contains identical quenching moieties, i.e., two Dabsyl moieties, pendant to a linking moiety that comprises the backbone of the 3,4-dimethamino benzoic acid linker 1.

In FIG. 2, a 3,5-dimethamino benzoic acid linker (not shown) is protected with a trifluoroacetyl group to form a 3-methamino-5-trifluoroacetylmethamino-benzoic acid 1b. The 3-methamino-5-trifluoroacetyl-methamino-benzoic acid 1b is reacted with Dabsyl chloride quencher 2a in a 1:1 or higher ratio to form an intermediate 4. The intermediate 4 is, in turn, ammonia deprotected and reacted with an NHS ester of BHQ-1 5 in a 1:1 or higher ratio to form the MCQ 6a. The MCQ 6a has two different quenching moieties, i.e., one Dabsyl moiety and one BHQ-1 moiety.

The linkers can also be multifunctional acyclic monomers. Suitable linkers include, for example, substituted amino acids such as ornithine and ornithine alkyl esters. Accordingly, the MCQ can comprise the following structure:

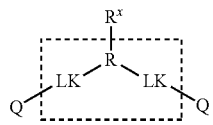

where each Q is a dark quencher that can be the same or different; where $R^x$ is a reactive functional group; where the remainder of the molecule (contained within the dashed line box) is a multivalent linking moiety where R is an acyclic moiety and each LK, independently, is a moiety that comprises one or more ester, urea, urethane, carbamate, amide, amine, phosphate, sulfonamide, ether, thioether, carbazide, hydrazone, silane, and siloxane linkages. In some embodiments, R is a hydrocarbon comprising up to ten carbon atoms.

FIG. 6 is illustrative of two quenchers being linked by reaction with a substituted amino acid. In FIG. 6, ornithine methyl ester 1c is reacted with Dabsyl NHS ester quencher 2b to form a methylester functional MCQ 13.

4.6 Dendritic MCQs

The multi-chromophoric quenchers can also be formed by reacting a dendritic polymer that is capable of reacting with an activated quencher molecule to form a linkage. Suitable dendritic polymers contain at least two reactive functional groups which can be, for example, any of the reactive functional groups set forth in section 4.4. However, if at least three reactive functional groups exist, then one reactive functional group can remain free to form future linkages to other substances (e.g., insoluble supports, probes for biomolecules, fluorescent dyes, etc. . . . ) Suitable dendritic structures can be formed, for example, by co-reacting monomeric linkers described in section 4.5 in a controlled fashion, using alternating protecting and deprotecting steps.

Accordingly, the MCQ can comprise the following formula:

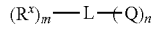

where m is a whole number greater than or equal to 1; where n is a whole number greater than or equal to 2; where each Q is a dark quenching moiety that can be the same or different; where L is a multivalent linking moiety comprising a dendritic backbone; and where each $R^x$ is a reactive functional group that can be the same or different. More particularly, in some embodiments m is 1, n is a number ranging from 3 to 8, and L comprises a dendritic polymer backbone.

The MCQ can be formed by a process comprising the following steps: (i) selecting $AB_x$ monomers, where each $AB_x$ monomer comprises one A moiety and x number of B moieties, where x is a whole number ranging from 2 to 4 and where said A and B moieties are co-reactive so that an A moiety on a given $AB_x$ monomer can react with a B moiety on a different $AB_x$ monomer to form a linkage; (ii) reacting the $AB_x$ monomers together, in one or more steps, to form a branched or multi-branched structure that comprises at least one unreacted A moiety and multiple unreacted B moieties; and (iii) reacting the branched or multi-branched structure with one or more terminating monomers, where each terminating monomer comprises a quencher moiety and at least one A moiety capable of reacting with a B moiety on the branched or multi-branched structure to form a linkage.

Alternatively, the MCQ can be formed by a process comprising the following steps: (i) selecting $AB_x$ monomers, where each $AB_x$ monomer comprises one A moiety and x number of B moieties, where x is a whole number ranging from 2 to 4 and where said A and B moieties are co-reactive so that an A moiety on a given $AB_x$ monomer can react with a B moiety on a different $AB_x$ monomer to form a linkage; (iii) reacting the ABx monomers with one or more quencher monomers to form linked quenchers, where each quencher monomer comprises at least one A moiety capable of reacting with a B moiety to form a linkage and iii) reacting the linked quenchers with an $AB_x$ monomer to form a larger linked quencher; and, optionally, (iv) repeating step (iii) one or more times using the larger linked quenchers.

The ABx monomers described above can be selected from a wide variety of multifunctional monomers. Illustrative monomers are multisubstituted benzoic acids, such as 3,5-dimethamino benzoic acid, and substituted amino acids, such as ornithine and ornithine alkyl esters.

For example, the MCQ generated can comprise one of the following structures:

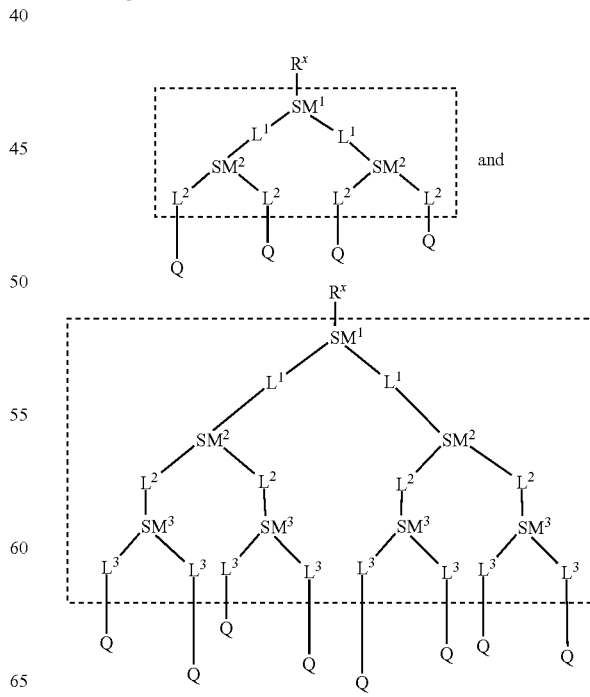

where each Q is a dark quenching moiety that can be the same or different, where $R^x$ is a reactive functional group, and where the remainder of the molecule (contained within the dashed line box) is a multivalent linking moiety where each $L^1$, $L^2$ and $L^3$ is a covalent bond or an intermediate linking group that can be the same or different, and can be formed by the reaction of A and B groups on an ABx monomer as described above, and each $SM^1$, $SM^2$ and $SM^3$ is a spacing moiety that can be the same or different.

FIG. 3 is illustrative. FIG. 3 shows two reaction routes. In the first route, a 3,5-dimethamino benzoic acid linker 1a is reacted first with at least two equivalents of MCQ 3b from FIG. 1. The product, MCQ 7, contains four identical quenching moieities, i.e., four Dabsyl moieties, pendent to a linking moiety (the reacted diamino benzoic acid backbone). In the second reaction route, a 3,5 dimethamino benzoic acid linker 1a is reacted with at least two equivalents of MCQ 6b. The product, MCQ 8, contains two types of quencher moieties, i.e., two Dabsyl moieties and two BHQ-1 moieities, pendent to a linking moiety (the reacted 3,5-dimethamino benzoic acid backbone).

4.7 Serial Branched Polymeric MCQs

The multi-chromophoric quenchers can also be formed by reacting a linear or branched polymeric linker that is capable of reacting with activated quencher molecules to form linkages. Suitable polymeric linkers include any polymer that has two or more reactive functional groups which can be, for example, any of the reactive functional groups set forth in section 4.4. However, if at least three reactive functional groups exist, then one reactive functional group can remain free to form future linkages to other substances (e.g., insoluble supports, probes for biomolecules, fluorescent dyes, etc. . . . ) Suitable linear or branched polymeric linkers can be formed, for example, from multifunctional branched and linear polyamines, polypeptides, polynucleotides, internucleotide analogs, polyolefins, polystyrenes, polyacrylates, polyamides, polyesters, polyurethanes, polyacrylamides and carbohydrates.

Accordingly, the MCQ can comprises the following formula:

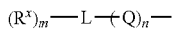

where m is a whole number greater than or equal to 1; where n is a whole number greater than or equal to 3; where each Q is a dark quenching moiety that can be the same or different; where L is a multivalent linking moiety comprising a linear or branched oligomeric or polymeric backbone; and where each $R^x$ is a reactive functional group that can be the same or different. More particularly, in some embodiments, m is 1, n is a number ranging from 3 to 8, and L comprises a linear or branched backbone of a polymer selected from polyamines, polypeptides, polynucleotides, internucleotide analogs, polyolefins, polystyrenes, polyacrylates, polyamides, polyesters, polyurethanes, polyacrylamides, and carbohydrates.

For example, the multivalent linking moiety (L) in the MCQ can be polypeptide backbone such as a polylysine backbone. An illustrative polylysine linker for making such an MCQ is shown below:

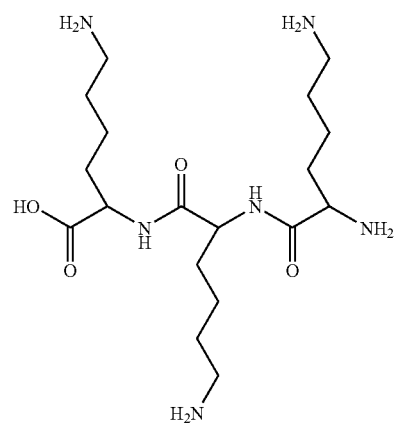 [SMILES: NCCCCC(N)C(=O)NC(CCCCN)C(=O)NC(CCCCN)C(=O)O]

A MCQ can be formed using the polylysine linker set forth above by reacting two or more of the reactive amino and carboxylic moieties with quenchers. For instance, a MCQ can be formed by reacting two or more of the reactive amino moieties with quenchers selected from sulfonylchloride substituted Dabsyl, NHS ester of BHQ-1, and mixtures thereof, in the same manner described in FIGS. 1-2 with respect to monomeric linkers. An MCQ so prepared, might have the following structure:

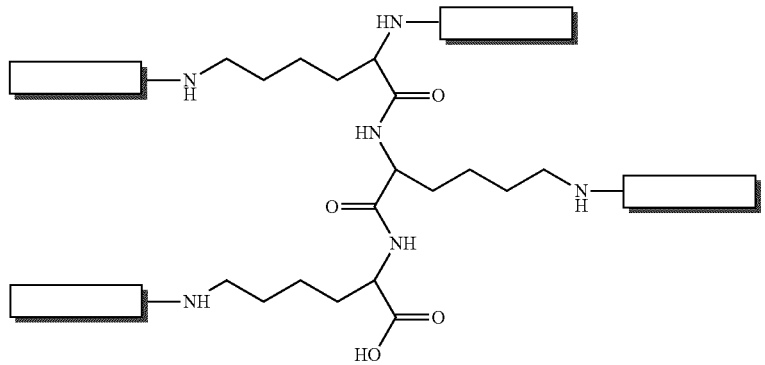

Alternatively, the multivalent linking moiety (L) in the MCQ can be a polynucleotide backbone such as a polymer of propargylamino DNA. An illustrative polymer of propargylamino DNA for use as a linker in an MCQ is shown below:

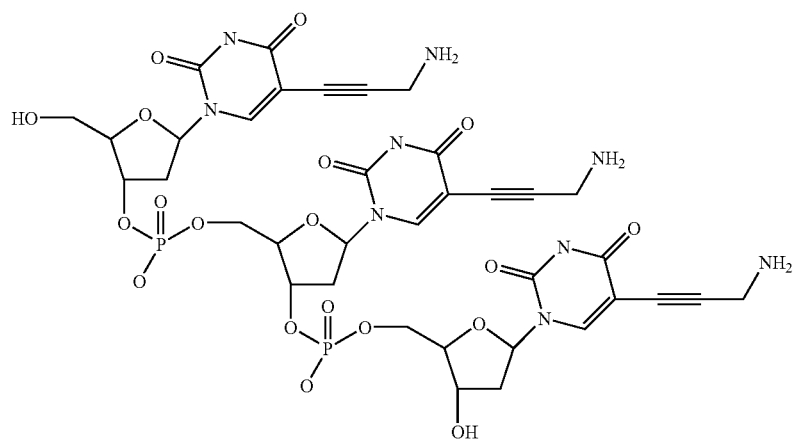 [SMILES: NCC#Cc1cn(C2CC(O)C(COP(=O)(O)OC3CC(n4cc(C#CCN)c(=O)[nH]c4=O)OC3COP(=O)(O)OC3CC(n4cc(C#CCN)c(=O)[nH]c4=O)OC3CO)O2)c(=O)[nH]c1=O]

A MCQ can be formed using such polymers by reacting two or more of the reactive amino moieties with dark quencher moieties. For instance, a MCQ can be formed by reacting two or more of the reactive amino moieties with sulfonylchloride substituted Dabsyl, NHS ester of BHQ-1, and mixtures thereof, in the manner described in FIGS. 1-2 with respect to monomeric linkers. Such MCQs would have the following structure:

A MCQ can be formed using the peptide nucleic acid linker set forth above by reacting two or more of the reactive amino and carboxylic moieties with dark quenchers. For instance, a MCQ can be formed by reacting two or more of the reactive amino moieties (i.e., those amino moieties positioned outside the peptide bonds) with quenchers selected from sulfonylchloride substituted Dabsyl, NHS ester of BHQ-1, and mix-

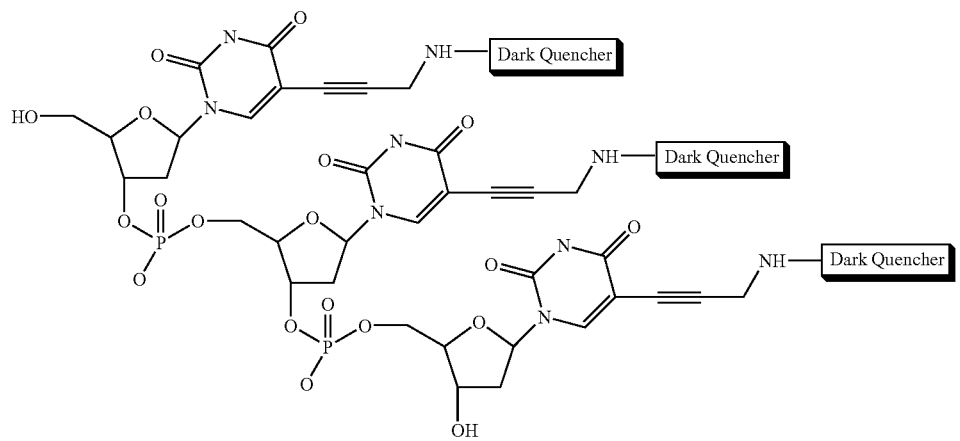 [SMILES: CNCC#Cc1cn(C2CC(O)C(COP(=O)(O)OC3CC(n4cc(C#CCNC)c(=O)[nH]c4=O)OC3COP(=O)(O)OC3CC(n4cc(C#CCNC)c(=O)[nH]c4=O)OC3CO)O2)c(=O)[nH]c1=O]

Alternatively, the multivalent linking moiety (L) in the MCQ can be a peptide nucleic acid (PNA) backbone. An illustrative peptide nucleic acid linker for making such an MCQ is shown below:

tures thereof, in the same manner described in FIGS. 1-2 with respect to monomeric linkers. An MCQ so prepared, would have the following structure:

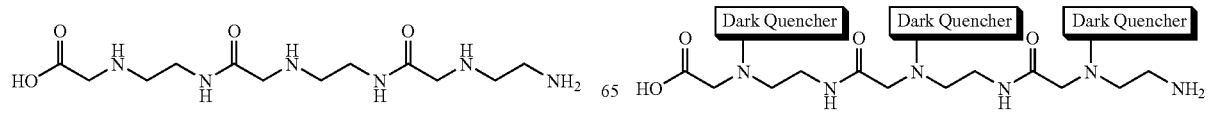

4.8 Linear Polymeric MCQs

The preceding multi-chromophoric quenchers (i.e., those set forth in sections 4.5, 4.6 and 4.7 above) comprise multiple quencher moieties pendent from a single linker moiety. However, the quenchers can themselves be multi-functional and, in such cases, the quenchers can co-react with one another, and/or other multifunctional linkers, to form repeat units of quencher moieties and multifunctional linkers within a polymer chain.

In embodiments where a linker is not employed, the quencher moieties are reacted directly with one another and the linking moiety is the product of the reactive functional groups on the linkers which can be, for example, any of the reactive functional groups set forth in section 4.4. Thus the linking moieties are typical chemical linkages, including, without limitation, ester, urea, urethane, carbonate, carbamate, amide, amine, phosphate, sulfonamide, ether, thioether, carbazide, hydrazone, silane, and siloxane linkages.

In those embodiments where a linker is employed, the linker can be any monomer that has at least two, and often only two, reactive functional groups. The reactive functional groups can be, for example, any of the reactive functional groups set forth in section 4.4. Linkers with only two reactive functional form polymers that generally begin and terminate with unreacted reactive functional groups. The unreacted functional groups can be used to bind the MCQ to other substances (e.g., insoluble supports, probes for biomolecules, fluorescent dyes, etc. . . . )

A wide variety of stable linking moieties are known in the art. The linking moieties can include single, double, triple and aromatic carbon-carbon bonds, nitrogen-nitrogen bonds, carbon-nitrogen, carbon-oxygen bonds and/or carbon-sulfur bonds, and may contain non-cyclic, cyclic and aryl structures. In some embodiments, the linking moieties have from 1-20 non-hydrogen atoms selected from the group consisting of C, N, O, S, Si and P and can be composed, for example, of one or more carbonyl, ester, urea, urethane, carbonate, carbamate, amide, carboxamide, amine, phosphate, sulfonamide, ether, thioether, carbazide, hydrazine, silane, and siloxane linkages.

Accordingly, the MCQs can comprise one of the following formula:

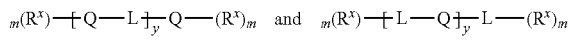

where m and y are whole numbers greater than or equal to 1; where each Q is a dark quenching moiety that can be the same or different; where each L is a multivalent linking moiety which can be the same or different; and where each $R^x$ is a reactive functional group, which can be the same or different. More particularly, in some embodiments, m is 1, y is a number ranging from 1 to 7, and each L is a moiety having from 1-20 non-hydrogen atoms selected from the group consisting of C, N, O, S, Si and P and can be composed, for example, of one or more ester, urea, urethane, amide, carbonate, carbamate, amine, phosphate, sulfonamide, ether, thioether, carbazide, hydrazone, silane, and siloxane linkages.

For example, quenchers to be linked can contain both amino and carboxylic bonds. In such cases, the quenchers can react with one another to form a series quenching moieties linked by amide bonds in a peptide like structure. An illustrative peptide like structure is shown below:

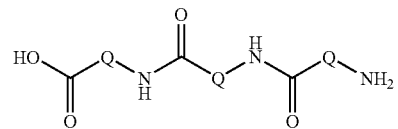

4.9 Conjugates Generally

The multi-chromophoric quenchers can be tethered to another molecule or substance through an attachment (i.e., multivalent linking moiety) formed by reacting a reactive functional group on the MCQ with the other substance. The conjugate formed comprises a carrier portion and at least one dark quenching portion, where each dark quenching portion comprises at least two dark quenching moieties, which can be the same or different, linked together by at least one multivalent linker moiety. Suitable carrier portions include one or more insoluble supports, one or more probes for biomolecules, one or more fluorescent dyes, and combinations thereof. For example, the conjugate can comprise one of the following structures:

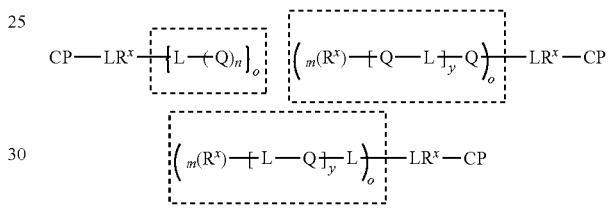

where n is a whole number greater than or equal to 2; where o and y are whole numbers greater than or equal to 1; where m is a whole number greater than or equal to 1; where CP is a carrier portion which comprises one or more insoluble supports, one or more probes for biomolecules, one or more fluorescent dyes, or a combination thereof; where the portion within the dashed square is the quenching portion, formed from a conjugated MCQ, wherein each Q is a dark quenching moiety that can be the same or different, and each L is a multivalent linking moiety that links multiple dark quenching moieties together; and where $LR^x$ is a multivalent linking moiety that links the carrier portion with the dark quenching portion. In most, but not all, embodiments, o is equal to 1.

The carrier portion in the conjugate can comprise an insoluble support. Suitable insoluble supports include cell surfaces, cellulose, dextran, liposomes, lipid bilayers, self assembling monolayers such as Langmuir-Blodgetee, micelles and latexes, organic polymers, copolymers and graft copolymers comprising units formed from olefin monomers, styrene, (meth)acrylates, hydroxyalkyl(meth)acrylates, acrylamide, and mixtures thereof, and inorganic materials such as glass, silica, controlled-pore-glass (CPG), and reverse-phase silica. The configuration of an insoluble support can take any form including particles, magnetic or nonmagnetic beads, membranes, frits, fibers, tubes, capillaries, slides, plates, micromachined chips, porous or non-porous surfaces, addressable arrays, and polynucleotide-immobilizing mediums.

Alternatively, or in addition, the carrier portion in the conjugate can comprise a probe for a biomolecule. Suitable probes include, for example, biomolecules that target the analyte and analogs thereof. For instance, the probe can be selected from amino acids, peptides, peptide analogs, proteins, polynucleotides, polynucleotide analogs, hormones, antigens, antibodies and combinations thereof.

Alternatively, or in addition, the carrier portion in the conjugate can comprise a fluorescent dye that forms a donor-acceptor energy transfer pair with at least one dark quenching moiety on the dark quenching portion. A tremendous advantage of the multi-chromophoric quenchers is that they can be used with a wide range of energy donor molecules. A vast array of fluorophores are known to those of skill in the art. A non-limiting list of exemplary donors that can be used with the MCQs include xanthenes (e.g., fluoresceins, rhodamines, and rhodols), cyanines, napthylamines, acridines, benzoxadiazoles, stilbenes, pyrenes, pyronines, coumarins, and porphyrins.

There is a great deal of practical guidance available in the literature for selecting appropriate donor-acceptor pairs for particular probes. See, e.g., Pesce et al., FLUORESCENT SPECTROSCOPY (Marcel Dekker, New York, 1971); White et al., FLUORESCENCE ANALYSIS: A PRACTICAL APPROACH (Marcel Dekker, New York, 1970); and the like. The literature also includes references providing exhaustive lists of fluorescent and chromogenic molecules and their relevant optical properties for choosing report-quencher pairs. See, e.g., Berlman, HANDBOOK OF FLUORESCENCE SPECTRA OF AROMATIC MOLECULES, $2^{ND}$ Ed. (Academic Press, New York, 1971); Griffiths, COLOUR AND CONSTITUTION OF ORGANIC MOLECULES (Academic Press, New York, 1976); Bishop, Ed., INDICATORS (Pergamon Press, Oxford, 1972); Haugland, HANDBOOK OF FLUORESCENT PROBES AND RESEARCH CHEMICALS (Molecular Probes, Eugene, 1992); Pringsheim, FLUORESCENCE AND PHOSPHORESCENCE (Interscience Publishers, New York, 1949); and the like. Further, there is extensive guidance in the literature for derivatizing reporter and quencher molecules for covalent attachment via common reactive groups that can be added to a nucleic acid. See, e.g., Haugland (supra); U.S. Pat. No. 3,996,345; U.S. Pat. No. 4,351,760. Thus, it is well within the abilities of those of skill in the art to choose an energy exchange pair for a particular application and to conjugate the members of this pair to a probe molecule or surface, such as, for example, a nucleic acid, peptide or other polymer.

Generally, the absorbance band of the MCQ substantially overlaps the fluorescence emission band of the donor. When the donor (fluorophore) is a component of a probe that utilizes donor-acceptor energy transfer, the donor fluorescent moiety and the quencher (acceptor) are preferably selected so that the donor and acceptor moieties exhibit donor-acceptor energy transfer when the donor moiety is excited. One factor to be considered in choosing the fluorophore-quencher pair is the efficiency of donor-acceptor energy transfer between them. Preferably, the efficiency of FRET between the donor and the MCQ is at least 50%, and even more preferably at least 98%. The efficiency of FRET can easily be empirically tested using methods known in the art. See, e.g., WO 01/86001.

4.10 Conjugates Comprising Probes Generally

The conjugates can be used as probes in assays for detecting a species in a mixture. Illustrative probes and assays are described below. The illustrative probes should not be interpreted as limiting the scope of probes that are possible and other useful probes will be apparent to those of skill in the art.

In general, to determine the concentration of a target molecule, such as, for example, a nucleic acid, it is preferable to first obtain reference data in which constant amounts of probe are contacted with varying amounts of target. The fluorescence emission of each of the reference mixtures is used to derive a graph or table in which target concentration is compared to fluorescence emission intensity. For example, a probe that: (a) hybridizes to a target-free nucleic acid ligand; and (b) has a stem-loop architecture with the 5' and 3' termini being the sites of fluorescent group and quencher labeling, can be used to obtain such reference data. Upon hybridization of the probe with target nucleic acid, the stem-loop straightens and the quencher separates from the fluorophore, permitting the fluorophore to emit. Such a probe gives a characteristic emission intensity profile in which the fluorescence emission increases as the target concentration increases in the presence of a constant amount of probe and nucleic acid ligand. Then, a test mixture with an unknown amount of target is contacted with the same amount of first nucleic acid and probe, and the fluorescence emission intensity is determined. The value of the fluorescence emission intensity is then compared with the reference data to obtain the concentration of the target in the test mixture.

Probes utilizing multi-chromophoric quenchers can be used in assays that detect a single target or in multiplex assays which detect one or more species in a mixture. The multi-chromophoric quenchers are easy to synthesize, can be made with broad absorbance characteristics, and increase sensitivity and decrease background from reporters. Therefore, the MCQs are particularly well suited for use in multiplex applications. In a typical multiplex analysis, two or more distinct species (or regions of one or more species) are detected using two or more probes, wherein each probe is labeled with a different fluorophore. Because MCQs can be formulated with a much broader absorbance range that conventional quenchers, MCQs make the design of multiplex assays easier by decreasing the investigation necessary to match reporter emission properties and the quencher absorbance properties.

For example, multiplex assays using nucleic acid probes with different sequence specifications have been described and are well known in the art. One such multiplex assay is used to determine whether an individual is homozygous wild-type, homozygous mutant or heterozygous for a particular mutation. Specifically, the assay uses a quenched-fluorescein energy transfer probe, such as a molecular beacon or Taqman probe, that recognizes the wild-type sequence and a quenched rhodamine energy transfer probe that recognizes a mutant allele. Each probe is quenched using a different quencher. The presence of only a fluorescein signal indicates that the individual is wild-type, the presence of a rhodamine signal indicates that the individual is a homozygous mutant, and the presence of both rhodamine and fluorescein signal is diagnostic of a heterozygote. However, in the past, different quenchers have been used with different fluorescent dyes to insure that the acceptor emission properties and the quencher absorbance properties overlap. Alternatively, dyes with emission within a narrower range have been used with a single quencher. The use of MCQs in such multiplex assays allows the same quencher to be used with fluorescent dyes having a wide range of emissions and, thus, increases the ease of designing and interpreting the assay.

Generally, there is only one carrier portion. However, in cases where, for example, the dark quenching portion is attached to a probe for a biomolecule the conjugate formed can be immobilized onto an insoluble support. If the immobilization occurs through reactive functional groups on the dark quenching portion, two carrier portions will be formed.

The conjugates, can be used in multiplex assays designed to detect and/or quantify substantially any species, including, for example, whole cells, viruses, proteins, (e.g., enzymes, antibodies, receptors), glycoproteins, lipoproteins, subcellular particles, organisms (e.g., Salmonella), nucleic acids (e.g., DNA, RNA and analogues thereof), polysaccharides, lipopolysaccharides, lipids, fatty acids, non-biological polymers and small molecules (e.g., toxins, pesticides, metabolites, hormones, alkaloids, and steroids).

4.11 Conjugates Comprising Small Molecule Probes

The Multi-chromophoric quenchers are useful, for example, in combination with fluorescent dyes, as components in small molecule probes. In one such design, a conjugate comprises a probe for a biomolecule, a fluorophore and a MCQ. Generally, the fluorescent dye and/or the MCQ is attached to the probe for a biomolecule by a linking group that is cleaved upon contact with an analyte. A target of interest, such as an enzyme, cleaves the MCQ, the fluorophore, or both, from the small molecule. Cleavage separates the fluorophore from the MCQ and, thereby, generates a detectable fluorescence in the system under investigation. Illustrative probes that can be used in such conjugates include, but are not limited to, small biomolecules such as toxins, drugs, pesticides, metabolites, hormones and steroids.

4.12 Conjugates Comprising Nucleic Acid Probes

The multi-chromophoric quenchers are also useful in combination with probes for analyzing nucleic acids (i.e., nucleic acid probes). Nucleic acid probes comprise a nucleic acid sequence complementary to a target nucleic acid. A nucleic acid probe can bear both a multi-chromophoric quencher and a fluorophore or, alternatively, two nucleic acid probes can be used in conjunction, the first nucleic acid probe being labeled with a MCQ and the second nucleic acid probe being labeled with a fluorophore.

Accordingly, a conjugate can comprise a MCQ, a nucleic acid and, optionally, a fluorescent dye. Such conjugates can be used as detection agents in a wide variety of DNA amplification/quantification strategies including, for example, 5'-nuclease assay, Strand Displacement Amplification (SDA), Nucleic Acid Sequence-Based Amplification (NASBA), Rolling Circle Amplification (RCA), as well as for direct detection of targets in solution phase or solid phase (e.g., array) assays.

When the conjugate comprises a MCQ and a nucleic acid only, it is used in conjunction with a nucleic acid probe labeled with a fluorophore. When the two nucleic acids are hybridized, either together or proximate to one another on neighboring complementary sequences on a third nucleic acid, the hybridization can be detected by observing the quenching of the fluorescence of the fluorophore on the fluorophore labeled nucleic acid by the MCQ on the proximate MCQ labeled nucleic acid.

When the conjugate comprises a nucleic acid, a MCQ and a fluorophore, the nucleic acid in the conjugate can assume any intramolecularly associated secondary structure. As examples, the secondary structure is a member selected from hairpins, stem-loop structures, pseudoknots, triple helices and conformationally assisted structures. In such embodiments, the preferred nucleic acids for use in the probe are single-stranded binding sequences. Generally, prior to hybridization to a complementary target sequence, the detector nucleic acid is in a conformation that allows donor-acceptor energy transfer between an attached fluorophore and MCQ. A change in fluorescence, however, is caused when the nucleic acid probe hybridizes with the target sequence and a change in conformation is caused by the hybridization. The change in conformation separates the energy transfer pair. The fluorophore, no longer quenched by the MCQ, emits a signal that can be detected in real time as an indicator of the presence of the target sequence.

Alternatively, a conjugate comprising a MCQ, a nucleic acid, and a fluorophore can operate by cleavage. Interaction with a target molecule cleaves the nucleic acid and, thereby, separates the proximate quencher and fluorophore to produce a signal.

In addition to their general utility in probes designed to investigate nucleic acid amplification, detection and quantification, such conjugates can be used in substantially any fluorescein based nucleic acid probe format For example, the conjugates can be incorporated into probe motifs, such as Taqman™ probes, molecular beacons, scorpion probes, sunrise probes, conformationally assisted probes, peptide nucleic acid (PNA) based light up probes, double strand specific DNA dyes and the like.

The nucleic acid probes used in the conjugates can be of any suitable size, and are preferably in the range of from about 10 to about 100 nucleotides, more preferably from about 10 to about 80 nucleotides and more preferably still, from about 20 to about 40 nucleotides. The precise sequence and length of a nucleic acid probe depends in part on the nature of the target polynucleotide to which it binds. The binding location and length can be varied to achieve appropriate annealing and melting properties for a particular embodiment. Guidance for making such design choices can be found in many art-recognized references.

Preferably, the 3'-terminal nucleotide of the nucleic acid probe is blocked or rendered incapable of extension by a nucleic acid polymerase. Such blocking is conveniently carried out by the attachment of a donor or acceptor moiety to the terminal 3'-position of the nucleic acid probe, either directly or by a linking moiety.

The nucleic acid can comprise DNA, RNA or chimeric mixtures or derivatives or modified versions thereof. Both the probe and target nucleic acid can be present as a single strand, duplex, triplex, etc.

The donor (fluorophore) groups and/or acceptor (MCQ) groups can be introduced at the 3'-terminus using an insoluble support modified with the desired groups. Additionally, donor and/or acceptor groups can be introduced at the 5'-terminus by, for example a derivative of the group that includes a phosphoramidite.

In the dual labeled nucleic acid probes (i.e., those containing both a MCQ and a fluorophore), the donor moiety is preferably separated from the MCQ by at least 10 nucleotides, and more preferably by at least 15 nucleotides. The donor moiety is preferably attached to either the 3'- or 5'-terminal nucleotide of the nucleic acid probe. The MCQ moiety is also preferably attached to either the 3'- or 5' terminal nucleotide of the nucleic acid probe. More preferably, the donor and acceptor moieties are attached to the 3'- and 5'- or 5' and 3'-terminal nucleotides of the nucleic acid probe, respectively, although internal placement of either or both is also useful.

This is illustrated, in part, by FIG. 4. In FIG. 4, a MCQ with an acid functional group 9a is reacted to form an NHS ester 9b. In one reaction route, the NHS ester 9a is reacted directly with a reactive amine on a polynucleotide to form a conjugate 10. Alternatively, in another reaction route, the NHS ester is reacted to form a phosphoramidite 11 which, in turn, is reacted with a reactive hydroxyl group on a oligonucleotide to form a conjugate 12.

4.13 Conjugates Comprising Nucleic Acid Analogs

Probes for nucleic acids, such as those described above, can also utilize nucleic acid analogs that hybridize with a nucleic acid target sequence. In other words, the nucleic acid probe used can be modified at the base moiety, sugar moiety, or phosphate backbone with other groups such as radioactive labels, minor groove binders, intercalculating agents, donor and/or acceptor moieties and the like. Therefore, in some embodiments, the conjugates comprises a nucleic acid analog and a MCQ. Alternatively, the conjugates comprise a nucleic acid analog, a MCQ and a fluorophore.

For example, the nucleic acid probe can comprise at least one modified base moiety which can be selected from the group including, but not limited to, 5-fluorouracil, 5-bromouracil, 5-chlorouracil, 5-iodouracil, hypoxanthine, xanthine, 4-acetylcytosine, 5-(carboxyhydroxymethyl)uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2,-dimethylguanine, 2-methyladenine, 2-methylguanine, 3-methylcytosine, 5-methylcytosine, $N^6$-adenine, 7-methylguanine, 5-methylaminomethyluracil, 5-methoxyaminomethyl-2-thiouracil, beta-D-mannosylqueosine, 5'-methoxycarboxymethyl-uracil, 5-methoxyuracil, 2-methylthio-$N^6$-iospentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl)uracil, (acp3)w, nitroindole, and 2,6-diaminopurine.

Alternatively, the nucleic acid probe can comprise at least one modified sugar moiety which can be selected from l-sugars, d-sugars, and locked nucleic acids (LNAs).

Alternatively, the nucleic acid probe can comprise at least one modified phosphate backbone selected from the group including, but not limited to, a peptide nucleic acid (PNA), a phosphorothioate, a phosphorodithioate, a phosphoramidothioate, a phosphoramidate, a phosphordiamidate, a methylphosphonate, and alkyl phosphotriester, and a formal acetal or analogs thereof.

Often, the conjugate comprises a PNA, due to the strong binding characteristics associated with PNA/nucleic acid interactions. As with nucleic acid probes, the conjugate containing the nucleic acid analog (e.g., PNA) can function as a molecular beacon, scorpion probe, sunrise probe, and conformationally assisted probes.

This is illustrated by FIG. 4. In FIG. 4, a MCQ with an acid functional group is reacted to form an NHS ester. In one reaction route, the NHS ester is reacted directly with a reactive amine on a PNA.

4.14 Conjugates Comprising Peptide Probes

Peptides that are labeled with a fluorophore and a multi-chromophoric quencher can be used in both in vivo and in vitro enzymatic assays. Accordingly, in some embodiments, useful conjugates include the following features: (i) a fluorophore; (ii) a MCQ; and (iii) a peptide with a cleavage or assembly recognition site for the enzyme. The conjugate is preferably of a length, orientation and conformation that permits donor-acceptor energy transfer between the fluorophore and the MCQ when the fluorophore is excited.

Such conjugates can be used to detect an enzyme such as a degradative enzyme (e.g., a protease). If the degree of the fluorescence emission intensity increases with time then this an indication of the presence of the enzyme.

Such conjugates are also be used to determine the amount of enzyme in a sample by determining the difference in the degree of reporter intensity before contact between the enzyme and the conjugate and after contact between the enzyme and the conjugate. The difference in the degree of fluorescence intensity, in comparison to a control sample, can be used to determine the amount of enzyme in the sample.

Such conjugates can also be used to determine whether a compound alters the activity of an enzyme, i.e., screening assays. To determine whether a compound alters the activity of an enzyme, the fluorescence of mixtures comprising the enzyme and conjugate are observed with and without the compound. If addition of the compound causes a change in the fluorescence properties, there is a strong likelihood that the compound is responsible for the change in enzyme activity.

Representative enzymes which can be used include, for example, trypsin, enterokinase, HIV-1 protease, prohormone convertase, interleukin-1b-converting enzyme, adenovirus endopeptidase, cytomegalovirus assembling, leishmanolysin, β-secretase for amyloid precursor protein, thrombin, rennin, angiotensin-converting enzyme, cathepsin-D and a kininogenase, and proteases in general.

Proteases play essential roles in many disease processes such as Alzheimer's, hypertension, inflammation, apoptosis, and AIDS. Accordingly, compounds that block or enhance their activity have tremendous potential as therapeutic agents. Screening compounds produced by combinatorial chemistry requires convenient enzymatic assays.

Preferably, the conjugate comprises a multi-chromophoric quencher and a fluorophore placed at the opposite ends of a short peptide chain containing a potential cleavage site. Proteolysis separates the fluorophore and MCQ, resulting in increased intensity in the emission of the donor fluorophore.

Such assays can be used to determine and characterize substrate cleavage sequences of proteases or for identifying proteases, such as orphan proteases. In some embodiments, a defined linker moiety amino acid sequence is replaced with one that contains a randomized selection of amino acids. A library of fluorescent MCQ/fluorophore bearing peptide conjugates, wherein the fluorophore and the MCQ are linked by a randomized peptide linker moiety can be generated. Screening the members of the library can be accomplished by measuring a signal related to cleavage, such as donor-acceptor transfer, after contacting the cleavage enzyme with each of the library members. A degree of donor-acceptor energy transfer that is lower than an expected amount indicates the presence of a linker sequence that is cleaved by the enzyme. The degree of donor-acceptor energy transfer can be determined as a function of the amount of fluorescence from the reporter.

In the conjugates, the donor and acceptor moieties are generally connected to the peptide through a linker moiety. The linker moiety, preferably, includes a peptide moiety, but can be or can include another organic molecular moiety. In a further embodiment, the linker moiety includes a cleavage recognition site specific for an enzyme or other cleavage agent of interest. A cleavage site in the linker moiety is useful because when a conjugate is mixed with the cleavage agent, the linker is a substrate for cleavage by the cleavage agent. Rupture of the linker moiety results in separation of the fluorophore and/or the MCQ. The separation is measurable as a change in donor-acceptor energy transfer resulting in an increase in donor fluorescence.

For example, when the cleavage agent of interest is a protease, the linker generally includes a peptide containing cleavage recognition site sequence for the protease. A cleavage recognition sequence for a protease is a specific amino acid sequence recognized by the protease during proteolytic cleavage. Many protease cleavage sites are known in the art, and these and other cleavage sites can be included in the linker moiety.

This is illustrated by FIG. 4. In FIG. 4, a MCQ with an acid functional group is reacted to form an NHS ester. In one reaction route, the NHS ester is reacted directly with a reactive amine on a peptide (e.g., protein).

4.15 Affinity Probes

Probes may be used in combination. For example, the conjugate may comprise a carrier portion that comprises a first probe for a biomolecule that has affinity for a second probe, where the second probe contains a fluorescent dye and has a higher affinity for a target molecule. Upon interaction with the target, the probes separate and the fluorescent dye on the second probe is no longer quenched by proximate quenching moieties on the first probe, thereby producing a detectable signal. Alternatively, the first probe can be the probe with a higher affinity for a target molecule.

4.16 Insoluble Support Immobilized Conjugates

The MCQs, as well as any conjugates comprising the same, can be immobilized on substantially any insoluble support. Suitable insoluble supports include, but not limited to cell surfaces, cellulose, dextran, liposomes, lipid bilayers, self assembling monolayers such as Langmuir-Blodgetee, micelles and latexes, organic polymers, copolymers and graft copolymers comprising units formed from olefin monomers, styrene, (meth)acrylates, hydroxyalkyl(meth)acrylates, acrylamide, and mixtures thereof, and inorganic materials such as glass, silica, controlled-pore-glass (CPG), and reverse-phase silica.

Preferred types of insoluble supports for the immobilization of conjugates comprising nucleic acid probes, for example, include, but are not limited to controlled pore glass, glass plates, polystyrene, avidin coated polystyrene beads, cellulose, nylon, acrylamide gel, and activated dextrane. These insoluble supports are preferred because of their chemical stability, ease of functionalization and well-defined surface area. Solid supports such as, contolled pore glass and non-swelling high cross-linked polystyrene are particularly preferred.

Generally, the insoluble support is tethered to the MCQ or conjugate by, for example, forming a bond between a reactive functional group on the surface of the support with a reactive functional group on the MCQ or conjugate, respectively. The reactive functional group on the conjugate can be on the MCQ or the carrier portion (e.g., a probe for a biomolecule or fluorescent dye). If the reactive functional group is on the MCQ in a conjugate, then the support forms a second carrier portion.

The bond between the insoluble support and the MCQ or conjugate is preferably a covalent bond. The conjugates can be immobilized on insoluble supports by ionic interactions, hydridization to an immobilized probe, hydrophobic interaction, or ligand/receptor interaction, using a variety of known procedures (U.S. Pat. No. 5,902,724, WO 98/04740). Covalent bonds between the MCQ or conjugate and the insoluble support include Schiff-base linkages (WO 01/09385) and phosphoramidite linkages (U.S. Pat. No. 6,013,789). Reactive functional groups which can be used in practicing the present invention are discussed in detail above and include amines, hydroxyl groups, carboxylic acids, carboxylic acid derivatives, alkenes, alkene halide, sulfhydryls, siloxanes, isocyanate, maleimide, haloacetyl, iodoacetamide, epoxide, alkyl halide, aldehyde, ketone, and acylazide. Support linked MCQ can contain an additional active group for probe conjugation by either automated stepwise synthesis or single step coupling to generate support linked MCQ conjugate. MCQ conjugates of the invention can be linked to an insoluble support through a cleavable linker including oxalate, succinate, quinone, diglycolate, alkylsilyl and disulfide. The ester linkages can be cleaved by basic reagents such as aqueous or gaseous ammonium hydroxide, anhydrous amines etc. The silyl linkers can be cleaved by base or fluoride reagents and sulfide linkers cleaved by reducing reagents such as dithiothreitol.

4.17 Methods for Enhancing and Widening Quencher Absorption

The multi-chromophoric quenchers enable one tune constructs to enhance and broaden quenching of reporter emissions. The MCQs optimize performance in ET probe applications. Novel quencher constructs can be designed to quench all fluorescent emissions with equal efficiency, eliminating costs associated with supplying multiple quencher products.

Generally, a method of synthesizing a multi-chromophoric dark quencher molecule with a broadened energy absorption profile comprises the following steps:
(i) selecting multiple dark quencher molecules that have different absorption spectrums, where said dark quencher molecules have at least one reactive functional group; and
(ii) linking said dark quencher molecules to a linking molecule that comprises reactive functional groups capable of reacting with the reactive functional groups on the dark quencher molecules to form linkages, where the absorption spectrum of the multi-chromophoric dark quencher molecule is broader than the absorption spectrum of its individual dark quencher molecule components.

Generally, a method of synthesizing a multi-chromophoric dark quencher molecule with an enhanced quenching capability comprising the following steps: (i) selecting multiple dark quencher molecules that have similar or identical absorption spectrums, where said dark quencher molecules have at least one reactive functional group; and (ii) linking said dark quencher molecules to a linking molecule that comprises reactive functional groups capable of reacting with the reactive functional groups on the dark quencher molecules to form linkages, where the quenching capability of the multi-chromophoric dark quencher molecule is greater than the quenching capability of its individual dark quencher molecule components.

These methods can be, and generally are, combined to generate multi-chromophoric quenchers that, simultaneously, broaden the absorption range and increase the total absorption within the absorption range. In other words, multiple types of quenching moieties can be employed to increase the absorption range and a multiple number of each type of quenching moiety can be used to increase the total absorptivity within the absorption range.

5.0 EXAMPLES

Aspects of the present teachings can be further understood in light of the following examples, which should not be construed as limiting the scope of the present teachings in any way.

5.1 Bis Dabsyl MCQ Synthesis and Probe Conjugation

N,N'bis dabsyl-ornithine methylester formation

Referencing FIG. 6, L-Ornithine methylester dihydrochloride 1c (109 mg, 0.03 mmol) and Dabsyl NHS 2b (366 mg, 1 mmol) were suspended in anhydrous dimethylformamide (4 mL). To this mixture, N,N'-diisopropylethylamine (0.2 mL) was added, and the reaction was stirred 16 hrs under Argon. The solvent was removed under vacuum and the crude product was triturated with dichloromethane (50 ml). The organic layer was washed with water (25 ml×2) and brine (25 ml), dried over sodium sulfate, filtered, and evaporated to yield the N,N' bis dabsyl-ornithine methylester 13 (251 mg, 78% yield).

N,N'-Bis Dabsyl-Ornithine Acid Formation

N,N' bis dabsyl ornithine methylester 13, (240 mg, 0.37 mmol) was mixed with a solution of lithium hydroxide (10% in water, 4 ml) and methanol (10 mL) and stirred overnight at 40° C. The reaction mixture was acidified with dilute hydrochloric acid and the precipitate was filtered off and dried to yield N,N'-bis dabsyl-ornithine acid 14a (210 mg, 90% yield).

N,N'-Bis Dabsyl-Ornithine NHS Ester Formation

N,N'-bis dabsyl ornithine acid 14a (63.4 mg, 0.1 mmol), O—(N-succinimidyl) tetramethyluronium tetrafluoro borate (40 mg, 0.13 mmol), and N,N'-diisopropylethylamine (0.1 ml) were stirred in anhydrous dimethylformamide (1.5 ml) for 1 hr. The solvent was removed and the product was partitioned between water and ethyl acetate (50 ml). The ethyl acetate extract was washed with water (25 mL×2), dried over sodium sulfate, filtered, and the solvent removed to give the crude compound. The crude mixture product was purified by column chromatography (silica gel, 4% methanol in dichloromethane) to give N,N'-bis dabsyl-ornithine NHS ester 14b (35.56% yield).

Probe Conjugation

A 3'-FAM polynucleotide (80,000 pM) derivatized with a 5'amino group was converted to its tetrabutylammonium salt by suspension in excess salt solution and concentrating to a solid. In a 1.5 ml eppendorf tube, the oligo was suspended in acetonitrile (100 ul) and then diluted with 200 ul of dichloromethane. A suspension of 3 mg of N,N'-bisdabsyl-ornithine NHS ester 14b in 100 ul of dichloromethane was added to the oligo suspension followed by 10 ul of diisopropylethylamine. The tube was capped and the reaction mixture heated at 50° C. for 5 hours. The solvent was removed under vacuum. The crude product was suspended in 100 mM TEAA buffer and loaded on a PD-10 column pre-equilibrated with 100 mM TEAA. The most rapidly eluting fraction, which contained the labeled oligo, was collected and concentrated to a solid. The 3'-FAM-5'-Bis dabcyl oligo was purified by RP HPLC. A control oligo probe with the same sequence and a mono dabcyl label was produced by the same procedure employing Dabcyl-NHS ester.

What is claimed:

1. A dark quencher construct comprising the following structural formula:

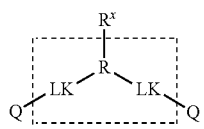

wherein:

each Q is diazoaryl dark quenching moiety selected from the group consisting of:

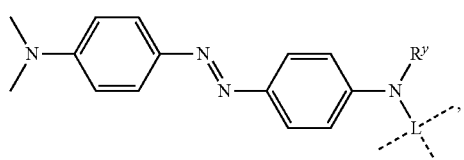

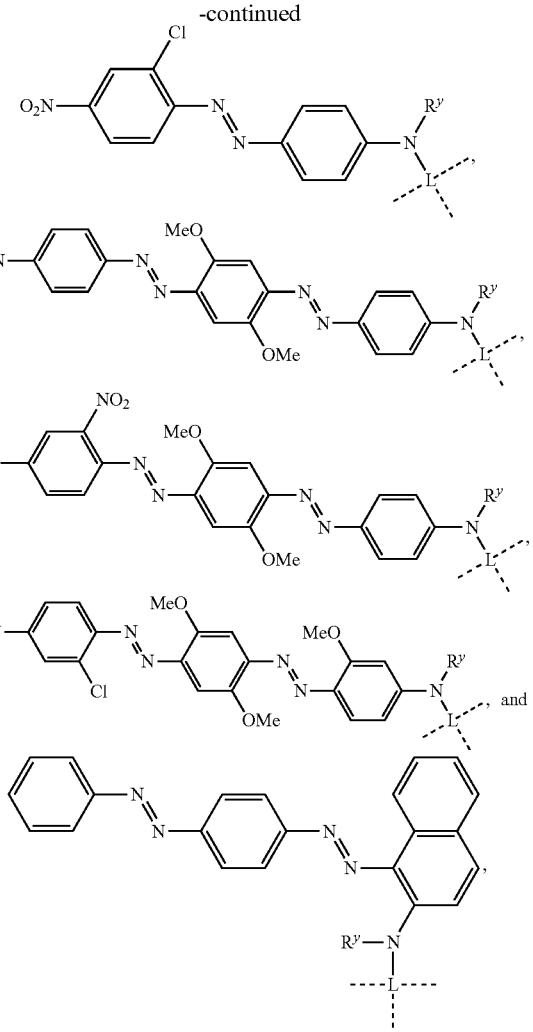

wherein the portion of the molecule contained within the dashed line box is a multivalent linking moiety L;

$R^y$ is H, $C_{1-4}$alkyl, aryl or arylalkyl;

R is an acyclic moiety;

each LK is an amide moiety; and $R^x$ is a reactive functional group.

2. The dark quencher construct of claim 1, wherein each multivalent linking moiety is independently a multivalent monomeric moiety.

3. The dark quencher construct of claim 1, further comprising a reactive functional group to facilitate attachment to one or more insoluble supports, probes for biomolecules, fluorescent dyes, or combinations thereof.

4. The dark quencher construct of claim 1, wherein the reactive functional group is carboxyl.

5. The dark quencher construct of claim 1, wherein L has between 1 and 20 non-hydrogen atoms selected from the group consisting of C, N and O.

6. The dark quencher construct of claim 1, wherein the construct is formed by reacting a substituted amino acid with two quenchers.

7. The dark quencher construct of claim 1, comprising the structure:

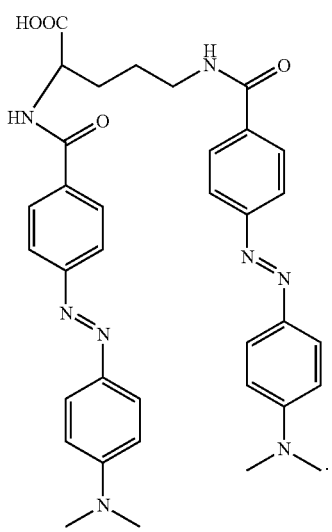 [SMILES: CN(C)c1ccc(/N=N/c2ccc(C(=O)NCCCC(NC(=O)c3ccc(/N=N/c4ccc(N(C)C)cc4)cc3)C(=O)O)cc2)cc1]

8. The dark quencher construct of claim 1, wherein all of the dark quenching moieties are the same.

9. A dark quencher construct comprising the following structural formula:

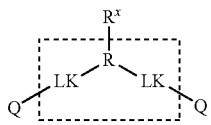

wherein:

each Q is diazoaryl dark quenching moiety selected from the group consisting of:

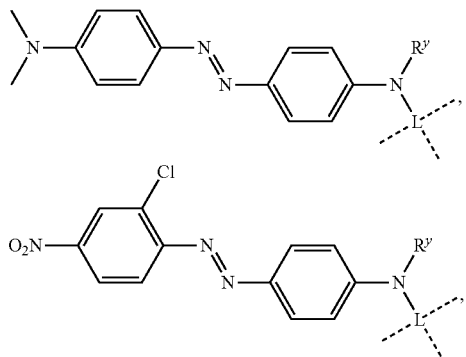

wherein the portion of the molecule contained within the dashed line box is a multivalent linking moiety L;

$R^y$ is H, $C_{1-4}$alkyl, aryl or arylalkyl;

R is an acyclic moiety;

each LK is independently selected from the group consisting of an ester, urea, carbonate, a carboxamide, a phosphate, an ether, a thioether, carbazide, hydrazine, a silane and a siloxane linkage; and $R^x$ is a reactive functional group.

10. The dark quencher construct of claim 8; wherein the reactive functional group is selected from the group consisting of an ester, hydroxyl, a haloalkyl, a dienophile, an aldehyde, a ketone, a sulfonyl halide, a thiol, an amine, a Michael donor, a Michael acceptor, an epoxide, a cyanuryl halide, phosphoramidite, a substituted hydrazine, and a substituted diazyl alkane.

* * * * *

UNITED STATES PATENT AND TRADEMARK OFFICE
CERTIFICATE OF CORRECTION

PATENT NO. : 8,586,718 B2  
APPLICATION NO. : 11/226069  
DATED : November 19, 2013  
INVENTOR(S) : Benson et al.

Page 1 of 1

It is certified that error appears in the above-identified patent and that said Letters Patent is hereby corrected as shown below:

Claims

• Column 32, Claim 10, Line 45 reads "The dark quencher construct of claim 8;"

• Column 32, Claim 10, Line 45 should read -- The dark quencher construct of claim 1; --

Signed and Sealed this
Eighth Day of March, 2016

Michelle K. Lee
*Director of the United States Patent and Trademark Office*